US011853874B2

(12) United States Patent
Boyer

(10) Patent No.: US 11,853,874 B2
(45) Date of Patent: Dec. 26, 2023

(54) PREDICTION AND REPORTING OF MEDICAL EVENTS

(71) Applicant: Covidien LP, Mansfield, MA (US)

(72) Inventor: Robert T. Boyer, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 394 days.

(21) Appl. No.: 16/165,666

(22) Filed: Oct. 19, 2018

(65) Prior Publication Data

US 2020/0125946 A1 Apr. 23, 2020

(51) Int. Cl.
*G06N 3/08* (2023.01)
*G16H 50/50* (2018.01)
*G16H 10/60* (2018.01)

(52) U.S. Cl.
CPC ............... *G06N 3/08* (2013.01); *G16H 10/60* (2018.01); *G16H 50/50* (2018.01)

(58) Field of Classification Search
None
See application file for complete search history.

(56) References Cited

U.S. PATENT DOCUMENTS

| | | | | |
|---|---|---|---|---|
| 6,658,287 B1 * | 12/2003 | Litt | ............ | G16H 50/20 600/544 |
| 10,226,187 B2 * | 3/2019 | Al-Ali | ............ | A61B 5/7275 |
| 2008/0214903 A1 * | 9/2008 | Orbach | ............ | A61B 5/165 600/301 |
| 2015/0157275 A1 * | 6/2015 | Swamy | ............ | A61B 5/0816 600/301 |
| 2016/0151021 A1 * | 6/2016 | Feng | ............ | A61B 5/6893 600/484 |
| 2016/0358500 A1 * | 12/2016 | Schlueter | ............ | G09B 5/02 |
| 2017/0182362 A1 * | 6/2017 | McLeod | ............ | A61B 5/1123 |

FOREIGN PATENT DOCUMENTS

CN 105792741 A * 7/2016 ........... A61B 5/0205

OTHER PUBLICATIONS

Eskaf, Khaled Ahmed. "Blood Glucose Level Prediction for Diabetic Patients using Intelligent Techniques." Order No. U567469 University of Salford (United Kingdom), 2011. Ann Arbor: ProQuest. Web. Aug. 3, 2023. (Year: 2011).*

* cited by examiner

*Primary Examiner* — Lena Najarian
(74) *Attorney, Agent, or Firm* — Fletcher Yoder, P.C.

(57) ABSTRACT

Methods, systems, and devices for event prediction are described. The method may include receiving real-time data associated with one or more measurements by a device. The method may also include updating one or more slope lines based on past instances of the real-time data and generating a feature vector based on the real-time data and the one or more slopes lines. The method may further include passing the first feature vector through an artificial neural network (ANN) and identifying an ANN output that acts as a predictive score. The method may also include predicting whether or not an event will occur based on the predictive score. In some cases, the predictive score may be passed through a voting mechanism, and the prediction of whether or not the event will occur may depend on an output of the voting mechanism.

18 Claims, 11 Drawing Sheets

PREDICTION AND REPORTING OF MEDICAL EVENTS

BACKGROUND

The following relates generally to event prediction, and more specifically to prediction and reporting of medical events.

In a healthcare facility such as a hospital, physiological parameters of the patient (e.g., heart rate, respiratory rate, blood pressure) may be monitored by one or more medical devices. Clinicians may remotely monitor the patient by accessing the patient data at a central nurse station or on any web enabled device connected to the network (e.g., smartphone or tablet).

A monitoring system may send an alarm once an adverse medical event has occurred (e.g., an apnea event or a code blue event), and clinicians may respond to the patient to address the underlying medical condition causing the alarm. Because monitoring systems are limited to detecting the occurrence of an adverse medical event, clinicians are limited to waiting for the event to occur before providing treatment, which may increase the risk to the patient.

SUMMARY

The described features generally relate to methods, systems, devices, or apparatuses that support prediction and reporting of medical events (e.g., apnea). A medical data server may receive physiological data associated with one or more measurements by a medical device. The physiological data may include respiration data (e.g., SpO2 and respiration rate) and may be real-time physiological data. The medical data server may update one or more slope lines based on past instances of the physiological data and generate a feature vector based on the one or more slope lines and a current instance of the physiological data for each relevant measurement type (e.g., one for SpO2 and one for respiration rate).

In some examples, the medical data server may pass the feature vector to an artificial neural network (ANN) and receive, from the ANN, a predictive score. Based on the predictive score, the medical data server may determine whether a medical event (e.g., a respiratory event, such as an apnea event) will occur. This determination may involve the medical data server receiving an output from a voting mechanism, through which the predictive score is passed, and determining the prediction based on the voting mechanism output. In some cases, multiple predictive scores may be passed into the voting mechanism.

A method of patient monitoring is described. The method may include receiving real-time physiological data associated with one or more measurements by a medical device, updating one or more slope lines based on past instances of the real-time physiological data, generating a first feature vector based on the real-time physiological data and the one or more slope lines, passing the first feature vector through an artificial neural network (ANN), identifying a first output from the ANN including at least a first predictive score, and predicting whether a medical event will occur at a future time based on the first predictive score.

An apparatus for patient monitoring is described. The apparatus may include a processor, memory in electronic communication with the processor, and instructions stored in the memory. The instructions may be executable by the processor to cause the apparatus to receive real-time physiological data associated with one or more measurements by a medical device, update one or more slope lines based on past instances of the real-time physiological data, generate a first feature vector based on the real-time physiological data and the one or more slope lines, pass the first feature vector through an artificial neural network (ANN), identify a first output from the ANN including at least a first predictive score, and predict whether a medical event will occur at a future time based on the first predictive score.

Another apparatus for patient monitoring is described. The apparatus may include means for receiving real-time physiological data associated with one or more measurements by a medical device, updating one or more slope lines based on past instances of the real-time physiological data, generating a first feature vector based on the real-time physiological data and the one or more slope lines, passing the first feature vector through an artificial neural network (ANN), identifying a first output from the ANN including at least a first predictive score, and predicting whether a medical event will occur at a future time based on the first predictive score.

A non-transitory computer-readable medium storing code for patient monitoring is described. The code may include instructions executable by a processor to receive real-time physiological data associated with one or more measurements by a medical device, update one or more slope lines based on past instances of the real-time physiological data, generate a first feature vector based on the real-time physiological data and the one or more slope lines, pass the first feature vector through an artificial neural network (ANN), identify a first output from the ANN including at least a first predictive score, and predict whether a medical event will occur at a future time based on the first predictive score.

In some examples of the method, apparatuses, and non-transitory computer-readable medium described herein, predicting whether the medical event will occur may include operations, features, means, or instructions for passing the first predictive score through a voting mechanism, and identifying an output from the voting mechanism.

Some examples of the method, apparatuses, and non-transitory computer-readable medium described herein may further include operations, features, means, or instructions for identifying one or more additional outputs of the ANN including one or more additional predictive scores, passing the one or more additional predictive scores through the voting mechanism, and predicting whether the medical event will occur based on the voting mechanism output, where the voting mechanism output may be based on the first predictive score and the one or more additional predictive scores.

Some examples of the method, apparatuses, and non-transitory computer-readable medium described herein may further include operations, features, means, or instructions for determining that a total number of predictive scores may be above a minimum threshold, where the total number of predictive scores includes the first predictive score and the one or more additional predictive scores, and predicting whether the medical event will occur based on determining that the total number of predictive scores may be above the minimum threshold.

In some examples of the method, apparatuses, and non-transitory computer-readable medium described herein, each predictive score of the first predictive score and the one or more additional predictive scores includes a positive vote or a negative vote.

Some examples of the method, apparatuses, and non-transitory computer-readable medium described herein may further include operations, features, means, or instructions for determining to pass the first predictive score and the one or more additional predictive scores through the voting mechanism based on the first predictive score including a positive vote.

In some examples of the method, apparatuses, and non-transitory computer-readable medium described herein, predicting whether the medical event will occur further may include operations, features, means, or instructions for determining that a percentage of positive votes may be above a threshold, and predicting that the medical event will occur based on the percentage of positive votes being above the threshold.

In some examples of the method, apparatuses, and non-transitory computer-readable medium described herein, predicting whether the medical event will occur further may include operations, features, means, or instructions for determining that a percentage of negative votes may be above a threshold, determining to cease passing new predictive scores through the voting mechanism, and predicting that the medical event will not occur based on the percentage of negative votes being above the threshold.

In some examples of the method, apparatuses, and non-transitory computer-readable medium described herein, predicting whether the medical event will occur further may include operations, features, means, or instructions for determining that the first predictive score and the one or more additional predictive scores may have a time-based order, determining that a number of consecutive predictive scores, including two or more of the first predictive score and the one or more additional predictive scores, include negative votes, determining that the number of consecutive predictive scores may be above a threshold, determining to cease passing new predictive scores through the voting mechanism, and predicting that the medical event will not occur based on determining that the number of consecutive predictive scores may be above the threshold.

Some examples of the method, apparatuses, and non-transitory computer-readable medium described herein may further include operations, features, means, or instructions for determining that the first predictive score and the one or more additional predictive scores may have a time-based order, where the first predictive score and the one or more additional predictive scores include time estimates, determining that at least one predictive score of a set of consecutive predictive scores, including two or more of the first predictive score and the one or more additional predictive scores, includes a lower time estimate than that of another predictive score of the set of consecutive predictive scores, and predicting that the medical event will occur based on determining that the at least one predictive score of the set of consecutive predictive scores includes the lower time estimate.

Some examples of the method, apparatuses, and non-transitory computer-readable medium described herein may further include operations, features, means, or instructions for determining an intercept associated with the first predictive score and the one or more additional predictive scores, where the first predictive score and the one or more additional predictive scores include time estimates, determining that the intercept may be within a time window, and predicting the medical event will occur based on determining that the intercept may be within the time window.

Some examples of the method, apparatuses, and non-transitory computer-readable medium described herein may further include operations, features, means, or instructions for transmitting, to a display, an indication that the medical event will occur based on predicting the medical event will occur at the future time.

In some examples of the method, apparatuses, and non-transitory computer-readable medium described herein, updating the one or more slope lines may include operations, features, means, or instructions for performing one or more linear regressions over one or time domains, where each time domain may be associated with a subset of the past instances of the real-time physiological data, generating one or more trend lines based on performing the one or more linear regressions, and determining slopes for each of the one or more trend lines.

In some examples of the method, apparatuses, and non-transitory computer-readable medium described herein, the one or more time domains include a set of overlapping time domains.

In some examples of the method, apparatuses, and non-transitory computer-readable medium described herein, the one or more time domains include a set of disjoint time domains.

In some examples of the method, apparatuses, and non-transitory computer-readable medium described herein, the medical event includes a respiratory event.

In some examples of the method, apparatuses, and non-transitory computer-readable medium described herein, the real-time physiological data includes end-tidal carbon dioxide (ETCO2) data, respiration rate data, pulse oximetry (SpO2) data, heart rate data, or a combination thereof.

A method of patient monitoring is described. The method may include a processor, memory in electronic communication with the processor, instructions stored in the memory and executable by the processor to cause the apparatus to, updating one or more slope lines based on past instances of the real-time physiological data, generating a first feature vector based on the real-time physiological data and the one or more slope lines, passing the first feature vector through an artificial neural network (ANN), identifying a first output from the ANN including at least a first predictive score, and predicting whether a medical event will occur at a future time based on the first predictive score.

An apparatus for patient monitoring is described. The apparatus may include a processor, memory in electronic communication with the processor, and instructions stored in the memory. The instructions may be executable by the processor to cause the apparatus to a processor, memory in electronic communication with the processor, instructions stored in the memory and executable by the processor to cause the apparatus to, update one or more slope lines based on past instances of the real-time physiological data, generate a first feature vector based on the real-time physiological data and the one or more slope lines, pass the first feature vector through an artificial neural network (ANN), identify a first output from the ANN including at least a first predictive score, and predict whether a medical event will occur at a future time based on the first predictive score.

Another apparatus for patient monitoring is described. The apparatus may include means for a processor, memory in electronic communication with the processor, instructions stored in the memory and executable by the processor to cause the apparatus to, updating one or more slope lines based on past instances of the real-time physiological data, generating a first feature vector based on the real-time physiological data and the one or more slope lines, passing the first feature vector through an artificial neural network (ANN), identifying a first output from the ANN including at least a first predictive score, and predicting whether a medical event will occur at a future time based on the first predictive score.

A non-transitory computer-readable medium storing code for patient monitoring is described. The code may include instructions executable by a processor to a processor, memory in electronic communication with the processor, instructions stored in the memory and executable by the processor to cause the apparatus to, update one or more slope lines based on past instances of the real-time physiological data, generate a first feature vector based on the real-time physiological data and the one or more slope lines, pass the first feature vector through an artificial neural network (ANN), identify a first output from the ANN including at least a first predictive score, and predict whether a medical event will occur at a future time based on the first predictive score.

A method of patient monitoring, the code including instructions executable by a processor to is described. The method may include receiving real-time physiological data associated with one or more measurements by a medical device, updating one or more slope lines based on past instances of the real-time physiological data, generating a first feature vector based on the real-time physiological data and the one or more slope lines, passing the first feature vector through an artificial neural network (ANN), identifying a first output from the ANN including at least a first predictive score, and predicting whether a medical event will occur at a future time based on the first predictive score.

An apparatus for patient monitoring, the code including instructions executable by a processor to is described. The apparatus may include a processor, memory in electronic communication with the processor, and instructions stored in the memory. The instructions may be executable by the processor to cause the apparatus to receive real-time physiological data associated with one or more measurements by a medical device, update one or more slope lines based on past instances of the real-time physiological data, generate a first feature vector based on the real-time physiological data and the one or more slope lines, pass the first feature vector through an artificial neural network (ANN), identify a first output from the ANN including at least a first predictive score, and predict whether a medical event will occur at a future time based on the first predictive score.

Another apparatus for patient monitoring, the code including instructions executable by a processor to is described. The apparatus may include means for receiving real-time physiological data associated with one or more measurements by a medical device, updating one or more slope lines based on past instances of the real-time physiological data, generating a first feature vector based on the real-time physiological data and the one or more slope lines, passing the first feature vector through an artificial neural network (ANN), identifying a first output from the ANN including at least a first predictive score, and predicting whether a medical event will occur at a future time based on the first predictive score.

A non-transitory computer-readable medium storing code for patient monitoring, the code including instructions executable by a processor to is described. The code may include instructions executable by a processor to receive real-time physiological data associated with one or more measurements by a medical device, update one or more slope lines based on past instances of the real-time physiological data, generate a first feature vector based on the real-time physiological data and the one or more slope lines, pass the first feature vector through an artificial neural network (ANN), identify a first output from the ANN including at least a first predictive score, and predict whether a medical event will occur at a future time based on the first predictive score.

A method of event prediction is described. The method may include receiving real-time data associated with one or more measurements by a device, updating one or more slope lines based on past instances of the real-time data, generating a first feature vector based on the real-time data and the one or more slope lines, passing the first feature vector through an artificial neural network (ANN), identifying a first output from the ANN including at least a first predictive score, and predicting whether an event will occur at a future time based on the first predictive score.

An apparatus for event prediction is described. The apparatus may include a processor, memory in electronic communication with the processor, and instructions stored in the memory. The instructions may be executable by the processor to cause the apparatus to receive real-time data associated with one or more measurements by a device, update one or more slope lines based on past instances of the real-time data, generate a first feature vector based on the real-time data and the one or more slope lines, pass the first feature vector through an artificial neural network (ANN), identify a first output from the ANN including at least a first predictive score, and predict whether an event will occur at a future time based on the first predictive score.

Another apparatus for event prediction is described. The apparatus may include means for receiving real-time data associated with one or more measurements by a device, updating one or more slope lines based on past instances of the real-time data, generating a first feature vector based on the real-time data and the one or more slope lines, passing the first feature vector through an artificial neural network (ANN), identifying a first output from the ANN including at least a first predictive score, and predicting whether an event will occur at a future time based on the first predictive score.

A non-transitory computer-readable medium storing code for event prediction is described. The code may include instructions executable by a processor to receive real-time data associated with one or more measurements by a device, update one or more slope lines based on past instances of the real-time data, generate a first feature vector based on the real-time data and the one or more slope lines, pass the first feature vector through an artificial neural network (ANN), identify a first output from the ANN including at least a first predictive score, and predict whether an event will occur at a future time based on the first predictive score.

DETAILED DESCRIPTION

Figure 1:
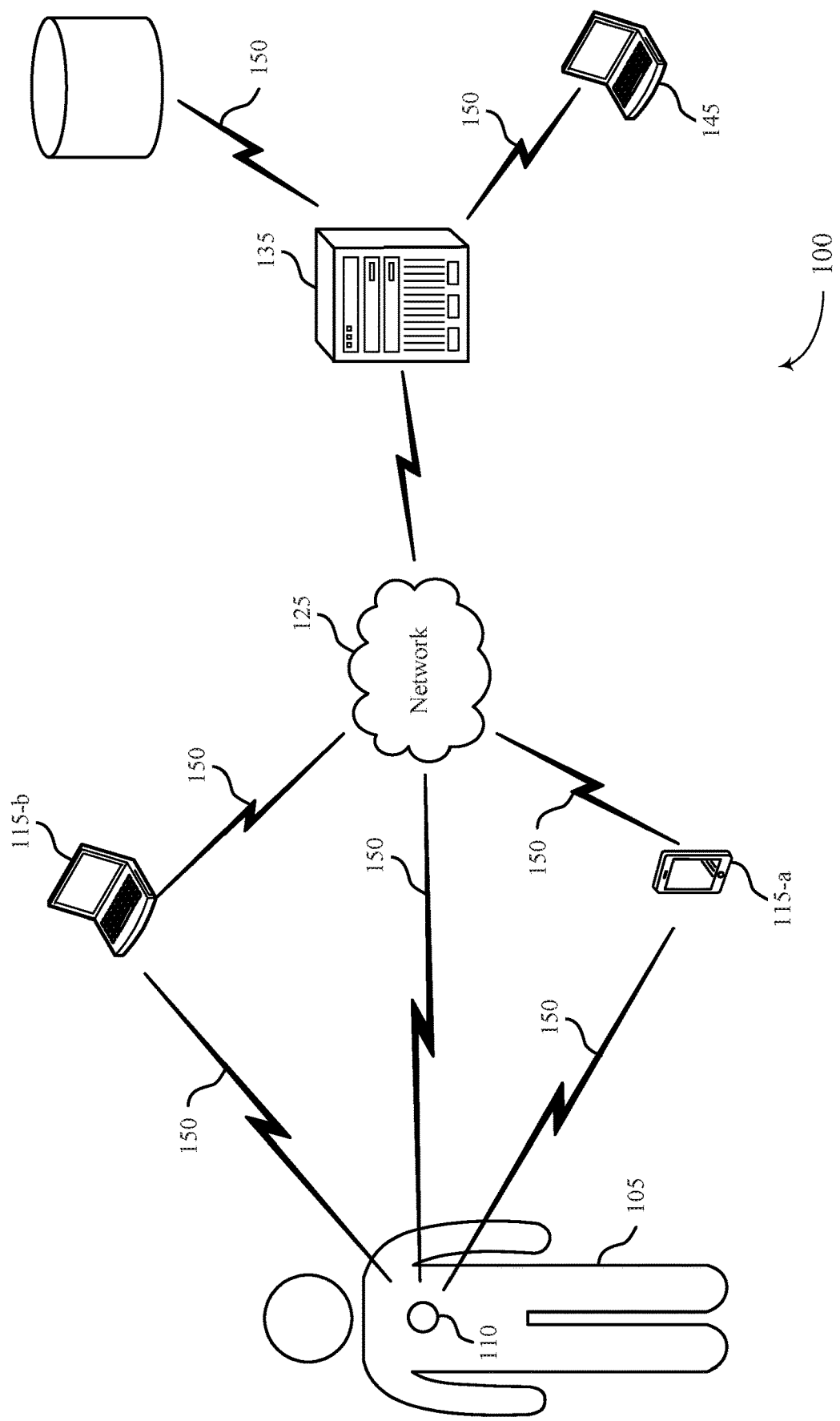
FIG. 1 illustrates an example of a system for patient monitoring that supports prediction and reporting of medical events in accordance with aspects of the present disclosure.

In some patient monitoring systems, a medical device may measure one or more physiological parameters of a patient and communicate real-time physiological data associated with the measurements to a central server (e.g., a central station) or some other downstream device or system. The downstream device may update one or more trend lines based on previous instances of the physiological data and generate a feature vector from one or more current instances of the physiological data (e.g., a current instance of pulse oximetry (SpO2) data and a current instance of respiration rate data) and the one or more trend lines. The feature vector may be passed through an artificial neural network (ANN) of the downstream device, which may output a predictive score (e.g., a positive vote, negative vote, or an estimate of time until a medical event occurs) to be passed through a voting mechanism of the downstream device. The voting mechanism may receive the predictive score and may predict whether or not a medical event will occur. The techniques described herein for predicting and reporting medical events (or other events) may enable increased preparation time for a medical event and may also enable more efficient time resource usage.

The medical device associated with the patient may transmit the physiological data to a central server. The physiological data may be data associated with respiration data (e.g., SpO2 data and/or respiration rate data) and may be real-time physiological data. In some cases, the physiological data may be compressed by the central server to encompass fewer data points (e.g., via averaging).

The central server may update one or more trend lines based on previous instances of the physiological data (e.g., compressed or uncompressed) and generate a feature vector. Each trend line may span a time domain relative to the current data point instances. Each time domain may overlap with other time domains or may be disjoint from the other time domains. Each trend line may have a corresponding slope. The central server may assemble the slopes of each trend line and the current data point instances together to generate the feature vector.

The feature vector may be passed through an ANN, which may output a predictive score that may be passed through a voting mechanism. The ANN may output the predictive score if the predictive score is a starting point predictive score (e.g., a positive predictive score received when a voting process is not occurring that triggers the voting process to start) or if a voting process is ongoing when the predictive score is generated. Elsewise, the predictive score may be discarded. If the predictive score is output, the predictive score may be stored until a later time (e.g., stored until a minimum number of predictive scores are output from the ANN during the voting process) or may be passed onto the voting mechanism (e.g., if the minimum number of predictive scores have been output from the ANN).

The voting mechanism may receive the predictive score and may predict whether or not a medical event will occur. The voting mechanism may further receive the predictive scores that have been stored during the current voting process. The prediction may be based on a certain number of predictive scores of the total number of predictive scores being positive predictive scores (e.g., positive votes). Additionally or alternatively, the prediction may be based on a certain number of predictive scores of the total number of predictive scores being negative predictive scores. Additionally or alternatively, the prediction may be based on a consecutive number of predictive scores (e.g., predictive scores that are output immediately after each other) being negative predictive scores. Additionally or alternatively, the prediction may be based on a consecutive number of predictive scores showing a downwards trend (e.g., decreasing monotonically) in an estimation of the time until a medical event will occur. Additionally or alternatively, the prediction may be based on a time-intercept associated with a certain number of predictive scores being within a time window.

If the voting mechanism determines that the medical event will occur (e.g., a positive prediction), the central server may transmit a prediction indication to a computing device. In some cases, the computing device may and may provide an alert that the medical event will occur. Additionally or alternatively, the computing device may provide a visual or auditory indication that the medical event will occur and may indicate when the medical event is likely to occur.

Aspects of the disclosure are initially described in the context of a wireless patient monitoring system. Aspects of the disclosure are further illustrated by and described with reference to apparatus diagrams, system diagrams, and flowcharts that relate to prediction and reporting of medical events.

FIG. 1 illustrates an example of a wireless patient monitoring system 100 in accordance with various embodiments of the present disclosure. The wireless patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wireless or wired communications links 150 to computing devices 115 or to a network 125.

The medical device 110 may include one or more sensors configured to collect a variety of physiological parameters as well as information related to the location and movement of the patient 105. For example, the medical device 110 may include a SpO2 sensor, a capnography sensor, a heart rate sensor, a ventilator, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be wirelessly transmitted to either the computing devices 115 or to the remote computing device 145 (via the network 125 and central station 135). In some cases, central station 135 may be a medical data server. Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

Computing device 115-a may be a wireless device such as a tablet, cellular phone, personal digital assistant (PDA), a dedicated receiver, or other similar device or a spatially distributed network of devices configured to receive signals from the medical device 110. Computing device 115-b may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. The central station 135 may also be in communication with various remote databases 140 where the collected patient data may be stored. In some cases, the remote databases 140 include electronic medical records (EMR) applications for storing and sharing patient data.

In accordance with various embodiments, methods and apparatuses are described for prediction and reporting of medical events. For instance, a medical data server (e.g., central station 135) may receive real-time physiological data associated with one or more measurements (e.g., SpO2 and/or respiration rate data) by a medical device (e.g., medical device 110). The medical data server may update one or more slope lines based on past instances of the real-time physiological data. The medical data server may further generate a feature vector based on the real-time physiological data. The medical data server may pass the feature vector through an ANN and identify a first output from the ANN that is a predictive score. The medical data server may predict whether a medical event (e.g., a respiratory event or a code blue) will occur at a time in the future based at least in part on the first predictive score.

Figure 2:
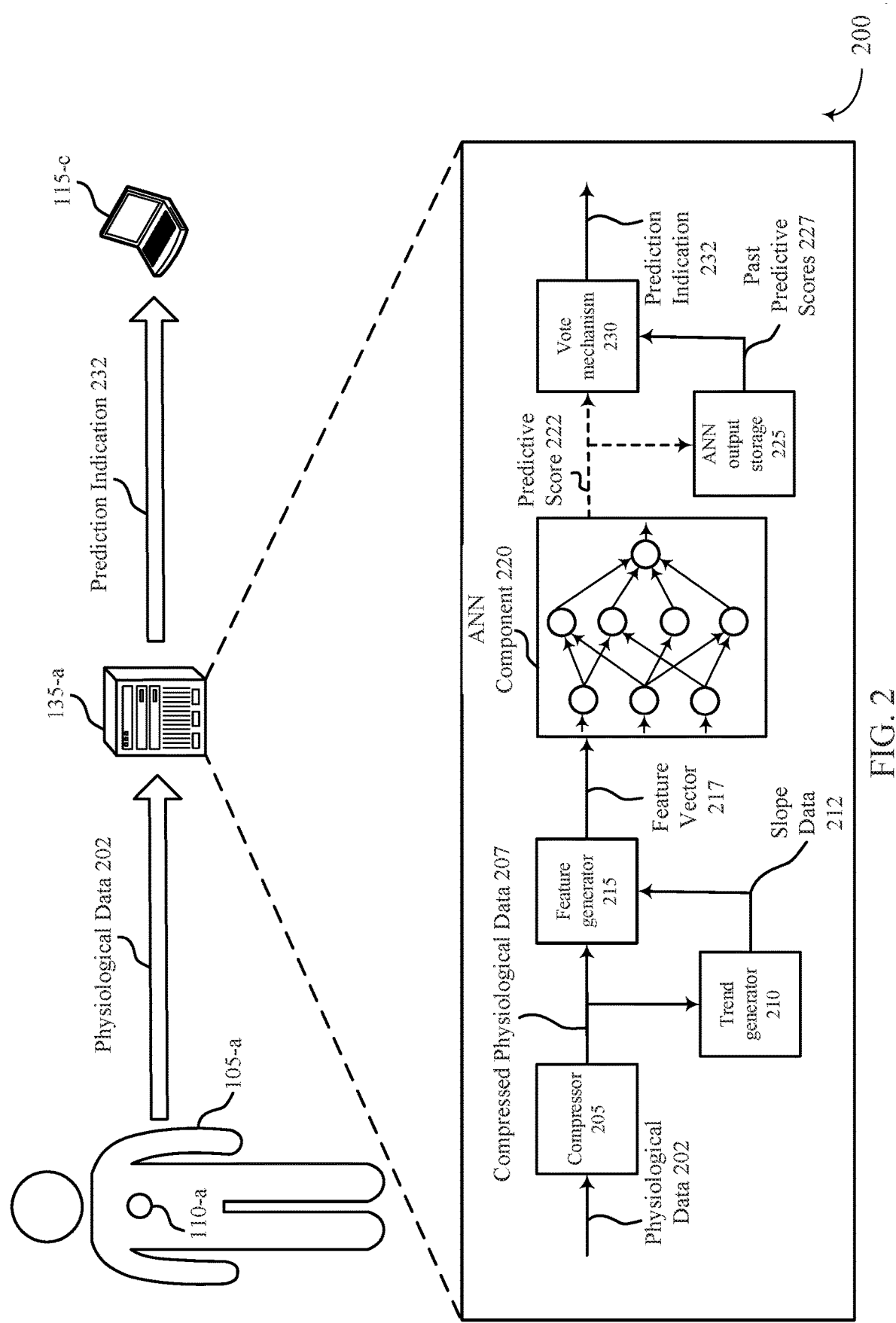
FIG. 2 illustrates an example of a system that supports prediction and reporting of medical events in accordance with aspects of the present disclosure.

FIG. 2 illustrates an example of a system 200 that supports prediction and reporting of medical events in accordance with aspects of the present disclosure. In some examples, system 200 may implement aspects of wireless patient monitoring system 100 and may include a patient 105-a wearing, carrying, or otherwise coupled with a medical device 110-a. System 200 may be in communication with medical data server 135-a and computing device 115-c. Medical data server 135-a may include a compressor 205, a trend generator 210, a feature generator 215, an ANN component 220, an ANN output storage 225, and a vote mechanism 230.

Medical device 110-a may transmit physiological data 202 to medical data server 135-a. Medical data server 135-a may be an example of aspects of central station 135. Physiological data 202 may include information associated with medical device 110-a. For instance, physiological data 202 may include SpO2 and respiration rate data. Other types of physiological data 202 (heart rate, end tidal $CO_2$ (ETCO2), $CO_2$, etc.) may be included or alternatively used without deviating from the scope of the present disclosure. In some cases, physiological data 202 may be from one or more sensors (e.g., pulse oximeter, capnograph, respirometer, and/or heart rate monitor sensors) associated with medical device 110-a. Physiological data 202 may be raw measurements or may be processed by medical device 110-a. Although physiological data 202 is being used for the present example, it should be understood that non-physiological data may also be used without deviating from the scope of the present disclosure.

Physiological data 202 may be received by the compressor 205. Compressor 205 may compress physiological data 202 (e.g., by averaging, median, mode, or other statistical operations) received over in particular time intervals (e.g., half-second intervals) and output compressed physiological data 207. Compressed physiological may contain a single data point representing data received during the period of time for each type of data received. For instance, assume that 10 data points are received for SpO2 and respiration rate over the first half of a second and 10 data points for SpO2 and respiration rate are received over the second half of a second. In such cases, compressor 205 may output a first compressed data point (e.g., labeled as at the half-second mark) representing an average of all of the SpO2 data points received in the first half of the second and may output a second data point (e.g., also labeled as at the half-second mark) representing an average of all of the respiration rate data points received in the first half of the second. Compressor 205 may, further, output a third compressed data point (e.g., labeled as at the one-second mark) representing an average of all of the SpO2 data points received in the second half of the second and may output a fourth data point (e.g., also labeled as at the one-second mark) representing an average of all of the respiration rate data points received in the second half of the second. In some cases, data points of physiological data 202 may or may not be spaced apart equally in time from each other and data points of compressed physiological data 207 may be spaced apart equally in time (e.g., according to the interval length) from each other.

Trend generator 210 may receive compressed physiological data 207. Trend generator 210 may perform a linear regression for one or more time domains covering current and past instances of compressed physiological data 207. Trend generator 210 may then output slope data 212, which may include a slope for each time domain and data type (a slope for SpO2 data in a first time domain, a slope for respiration rate in the first time domain, a slope for SpO2 data in a second time domain, etc.). In some cases, the time domains may overlap. For instance, a first time domain may include all past instances of compressed physiological data 207 within a minute before the current instance and a second time domain may include all past instances of compressed physiological data 207 within two minutes before the current instance. In other cases, the time domains may be disjoint from each other. For instance, a first time domain may include all past instances of compressed physiological data between the time of the current instance and the minute before the current instance, and a second time domain may include all past instances of compressed physiological data 207 between one minute before the current instance and two minutes before the current instance. In cases where compressor 205 is not used, trend generator 210 may instead receive and utilize physiological data 202. Trend generator 210 may further output an intercept associated with each slope of the slope data 212.

Feature generator 215 may receive compressed physiological data 207 and slope data 212 and output a feature vector 217 including compressed physiological data 207 and slope data 212. For instance, if compressed physiological data 207 includes SpO2 data and respiration rate data and if slope data 212 includes four slopes (e.g., a first slope for SpO2 in a first time domain, a second slope for SpO2 in a second time domain, a third slope for respiration rate in the first time domain, a fourth slope for respiration rate in the second time domain), then the feature vector may include six elements (e.g., a first element for the most current instance of compressed SpO2 data, a second element for the most current instance of compressed respiration rate data, and four elements for the four slopes). In general, the feature vector may contain one element for each relevant data type (where there are m data types) and mn elements for relevant slopes (e.g., where linear regressions are performed over n time domains). In cases where compressor 205 is not used, feature generator 215 may instead receive and utilize physiological data 202. In some cases, feature vector 217 may, additionally or alternatively, include intercept information (e.g., the intercept information output by trend generator 210).

Artificial neural network (ANN) component 220 may receive feature vector 217 and may or may not output a predictive score (e.g., a current predictive score 222) after passing the feature vector through an ANN. The ANN component 220 may have been previously trained (e.g., using supervised learning) on labeled examples of combinations of trends and current instances of compressed physiological data 207 or physiological data 202 and the resulting occurrence (or non-occurrence) of a medical event. As a result of the training, the ANN component 220 may generate a predictive score (e.g., via classification) on new instances of compressed physiological data 207 or physiological data 202 (e.g., if compressor 205 is not utilized). The predictive score may be a binary vote (e.g., a positive or negative vote) or may be a number conveying the likelihood of a medical event (e.g., a number on a scale between 1 to 5, where 1 is a negative vote, 2 is an unsure vote leaning negative, 3 is an undecided vote, 4 is an unsure vote leaning positive, and 5 is a positive vote). In other cases, the predictive score may be a time estimate, where the time estimate may be an estimated time until the medical event is predicted to occur. For instance, the predictive score may indicate a prediction that the medical event will occur in 5 minutes from the time associated with the most current instance of compressed physiological data 207 or physiological data 202 (e.g., in cases where the compressor 205 is not utilized). The ANN may be implemented into the software, hardware, or firmware of the medical data server 135-a.

ANN component 220 may output a current predictive score 222 (e.g., a predictive score corresponding to the current physiological data point) if the current predictive score 222 is a starting point predictive score triggering a voting process (e.g., a first positive predictive score received while a voting process is not ongoing) or if a voting process is currently in progress. If the current predictive score 222 is a starting point predictive score, medical data server 135-a may trigger a voting process (e.g., ANN component 220 may begin outputting all predictive scores). If the current predictive score 222 is not a starting point predictive score or is not received while a voting process is currently in progress, ANN component 220 may discard the current predictive score 222 or otherwise not output the current predictive score 222. In other cases, ANN component 220 may always output the current predictive score 222.

If ANN component 220 outputs the current predictive score 222, the current predictive score may be passed along to the ANN output storage 225 or the vote mechanism 230. Such a determination may be based on whether a minimum number of predictive scores since the voting process began (e.g., since a starting point predictive score was output by ANN component 220) has been output by ANN component 220. For instance, if the number of output predictive scores is less than a threshold minimum number, then the current predictive score may be passed along to the ANN output storage 225 to be used at a later instance at time (e.g., when the number of the total number of predictive scores output during the voting process is equal to or above the threshold). Alternatively (e.g., if the threshold number of predictive scores has been reached), the starting point predictive score may be passed to vote mechanism 230. In some cases, the current predictive score 222 may be always passed along to the ANN output storage 225, the vote mechanism 230, or both.

If the current predictive score 222 is passed to the vote mechanism 230 (e.g., because the number of predictive scores output by the ANN component 220 is equal to or above the threshold), ANN output storage 225 may output past predictive scores 227 to vote mechanism. The past predictive scores 227 may, for example, include all of the previous predictive scores received by ANN output storage 225 since the voting process began (e.g., the starting point predictive score and other predictive scores). In some cases, the ANN output storage 225 may not be utilized and the vote mechanism 230 may operate using only the current predictive score (e.g., if the current predictive score 222 is positive, then a prediction indication 232 may be sent; elsewise, the prediction indication 232 may not be sent).

Once the vote mechanism 230 receives the current predictive score 222 and the one or more predictive scores 227 (if applicable), the vote mechanism 230 may determine a prediction of whether or not a medical event (e.g., a respiration event, such as apnea) will occur (e.g., via a logical hysteresis). For instance, the vote mechanism 230 may determine that a certain percentage of the total predictive scores (e.g., current predictive score 222 and/or the one or more predictive scores 227) output during the voting process are positive predictive scores (e.g., positive binary votes or predictive scores associated with a number above a threshold) and determine that the medical event will occur. Additionally or alternatively, the vote mechanism 230 may determine that a certain percentage of the total predictive scores output during the voting process are negative predictive scores (e.g., negative binary votes or predictive scores associated with a number below a threshold) and determine that the medical event will occur. If both the percentages of negative and positive predictive scores are above their respective thresholds, then the vote mechanism 230 may determine that the medical event will not occur. Additionally or alternatively, the vote mechanism 230 may determine that a consecutive number of predictive scores (e.g., predictive scores that are output immediately after each other) are negative (e.g., negative binary votes or predictive scores each associated with a number below a threshold). Additionally or alternatively, the vote mechanism 230 may be an ANN and each predictive score may be an element of a feature vector passed into the ANN. Although the present example is determining whether a medical event will or will not occur, it should be understood that the methods disclosed herein may also predict whether or not other types of events may occur (e.g., if using non-physiological data).

In cases where the current predictive score 222 and the one or more predictive scores 227 are time estimates, the vote mechanism 230 may, additionally or alternatively, use other methods to determine a prediction of whether or not a medical event (e.g., a respiration event, such as apnea) will occur. In one example, if each subsequent predictive score of a consecutive number of the total predictive scores (e.g., the current predictive score 222 and/or the one or more predictive scores 227) indicates a lower time estimate until the medical event occurs (e.g., the first predictive score predicts five minutes until a medical event occurs, the second predictive score, following the first, predicts three minutes until a medical event occurs, and the third predictive score, following the second, predicts one minute until a medical event occurs), the vote mechanism may determine that the medical event will occur. Additionally or alternatively, if the time estimates associated with each subsequent predictive score of a consecutive number of predictive scores is approximately the same or increasing with each subsequent predictive score (e.g., a first predictive score predicts three minutes until a medical event occurs, the following predictive score predicts four minutes, and the following predictive score predicts five minutes), the vote mechanism 230 may determine that the medical event will not occur.

Additionally or alternatively, the vote mechanism 230 may determine a slope and an intercept with respect to the time instance of the compressed physiological data 207 (e.g., or physiological data 202 when compressor 205 is not utilized) associated with each time estimate and predict the medical event based on the slope and/or the intercept (e.g., the time-instance intercept). For instance, if a time estimate of 300 seconds is determined from an instance of compressed physiological data 207 at time $t_1$ and a time estimate of 60 seconds is determined from an instance of compressed physiological data 207 at time $t_2$, the vote mechanism may determine a slope $$M = \frac{60 - 300}{t_2 - t_1}$$

and intercept $$c = t_2 - \frac{60}{M}.$$

Linear regression may be utilized in cases where there are more than two predictive scores. Once the vote mechanism 230 determines the intercept, the vote mechanism may determine if the intercept is within a certain window after the time instance associated with the current predictive score 222. For instance, if the time instance is at 60 seconds, the time window is 120 seconds, and the intercept is at 150 seconds, then the vote mechanism 230 may determine a prediction that the medical event will occur (e.g., because (60+120)>150). Alternatively, if the time window is 60 seconds, then the vote mechanism 230 may determine that the medical event will not occur (e.g., because (60+60) <150).

If the vote mechanism 230 determines that the medical event will occur, the vote mechanism may output a prediction indication 232 which may be received by computing device 115-c and/or EMR. Alternatively, if the vote mechanism 230 determines that the medical event will not occur, the one or more predictive scores 227 may be discarded from the ANN output storage 225 and the voting process may not begin again until a new starting point predictive score is received. Alternatively, if the vote mechanism 230 is unable to determine whether or not a medical event will occur or not, the current predictive score 222 may be sent to the ANN output storage 225 and the voting process may continue with the next predictive score output by the ANN component 220.

Upon receiving the prediction indication 232, computing device 115-c may perform a number of tasks. In some cases (e.g., where computing device 115-c is an alert annunciation system), computing device 115-c may provide an alert that the medical event will occur. In other cases, the computing device 115-c may provide a visual and/or auditory indication (e.g., provide information a display) that may indicate that the medical event will occur and/or when the medical event will occur. In one example, computing device 115-c may indicate that there is a certain chance that the medical event will occur in the next 30 seconds, a separate chance that the medical event will occur in 60 seconds, etc. In another example, computing device 115-c may, for instance, indicate that the medical event is likely to occur within the next minute. In some cases, the visualization or alarm severity may change over time as the duration of the predictive medical event increases.

An advantage of utilizing a voting mechanism with multiple votes is that it may increase specificity (e.g., a proportion of a number of negative predictions, that a medical event will not occur, to a total number of predictions (positive or negative) in which the medical event did not occur) and/or sensitivity (e.g., a proportion of a number of positive predictions, that a medical event will occur, to a total number of predictions (positive or negative) in which the medical event occurred). Further, voting mechanisms that utilize multiple votes may increase the robustness of a prediction (e.g., predictions that use multiple votes may be less subject to instances where a state changes rapidly in the short term).

Figure 3A:
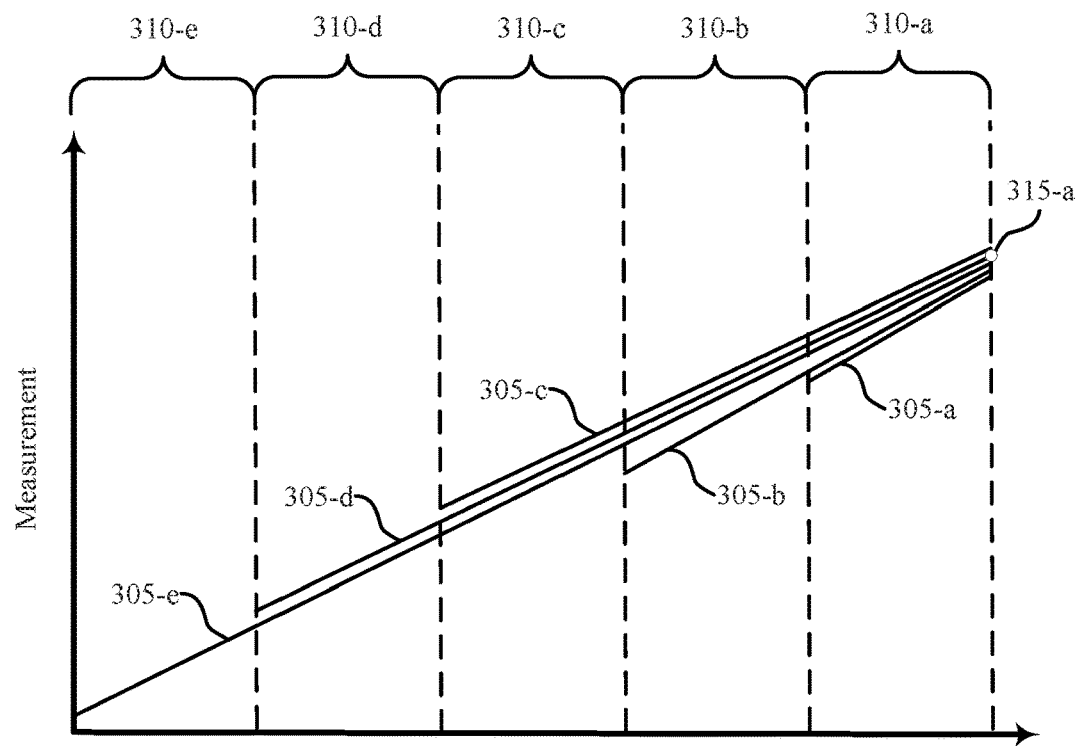
FIGS. 3A and 3B illustrate examples of trend line configurations that support prediction and reporting of medical events in accordance with aspects of the present disclosure.
Figure 3B:
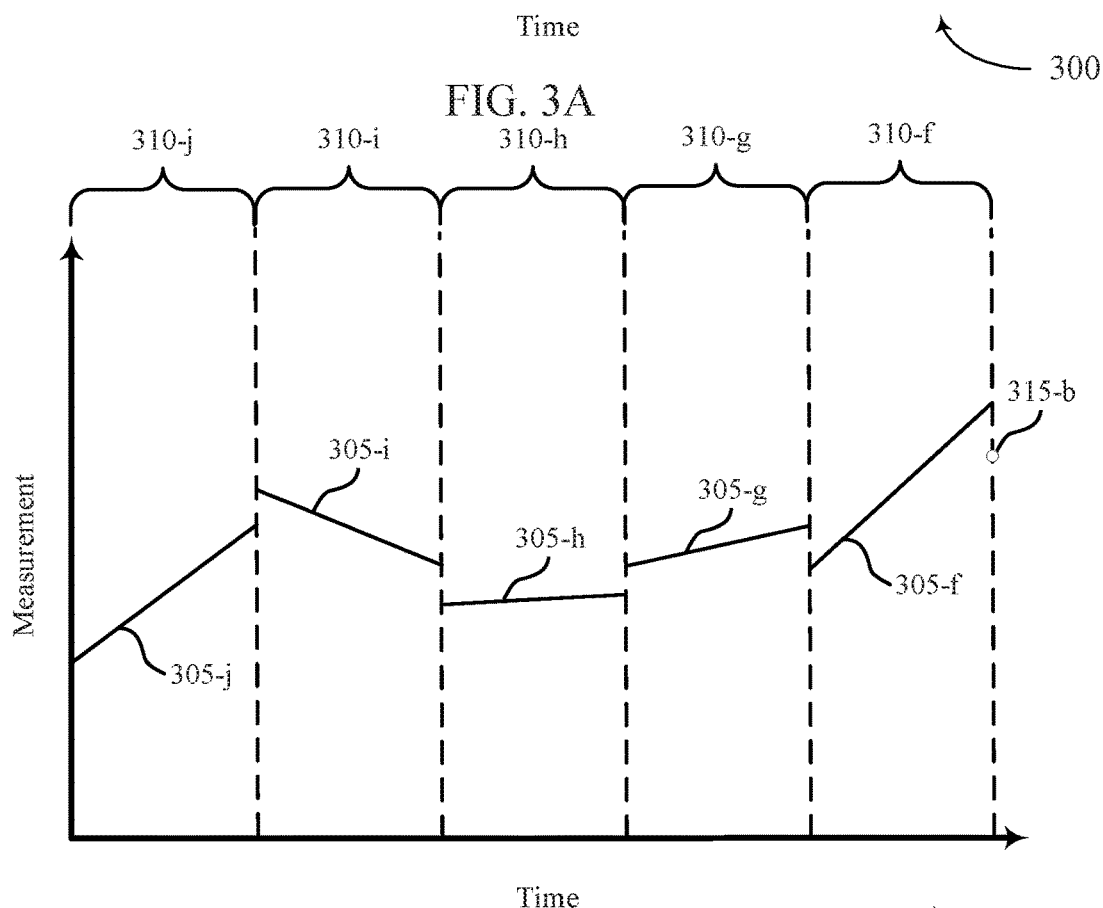

FIGS. 3A and 3B illustrate examples of trend line configurations 300 and 301 that support prediction and reporting of medical events in accordance with aspects of the present disclosure. In some examples, trend line configurations 300 and 301 may implement aspects of wireless patient monitoring system 100. Trend line configurations 300 and 301 may be examples of aspects of system 200 and may be utilized by a trend generator 210.

In trend line configurations 300 and 301, the y-axis may represent data (e.g., respiration rate data or SpO2 data) and the x-axis may represent time. Each trend line 305 may have a corresponding slope. A trend generator 210 may output these slopes (e.g., as slope data 212) and a feature generator 215 may receive these slopes. The feature generator 215 may use these slopes and a current physiological data value 315-a to generate a feature vector. If there are multiple types of data being utilized (e.g., respiration rate data and SpO2), the feature vector may include the slopes and current physiological data value of each.

In trend line configuration 300, multiple trend lines 305 may span over one or more time intervals 310 in an overlapping fashion. For instance, trend line 305-a may span over time interval 310-a. As such, the time domain of trend line 305-a may be time interval 310-a. Trend line 305-c may, alternatively, span over time interval 310-a, time interval 310-b, and time interval 310-c. As such, the time domain of trend line 305-c may be the time spanned by time intervals 310-a, 310-b, and 310-c.

In trend line configuration 301, multiple trend lines 305 may span over one time interval 310 in a disjoint fashion.

For instance, trend line 305-*f* may span a different time domain than trend line 305-*g*, although in some instances trend line 305-*f* and 305-*g* may share an endpoint.

While each trend line 305 in the present example spans one time interval 310, it should be noted that, in some examples, each trend line 305 may span a variable number of time intervals. For instance, in an example with five time intervals 310 and four trend lines 305, three of trend lines 305 may each span one time interval 310 and one of the trend lines 305 may span two time intervals disjoint from the others. It should also be noted that, in some instances, that combinations of trend line configuration 300 and 301 may be used without deviating from the scope of the present disclosure. For instance, some of the time domains of trend lines 305 may overlap and some of them may be completely disjoint from others.

Figure 4:
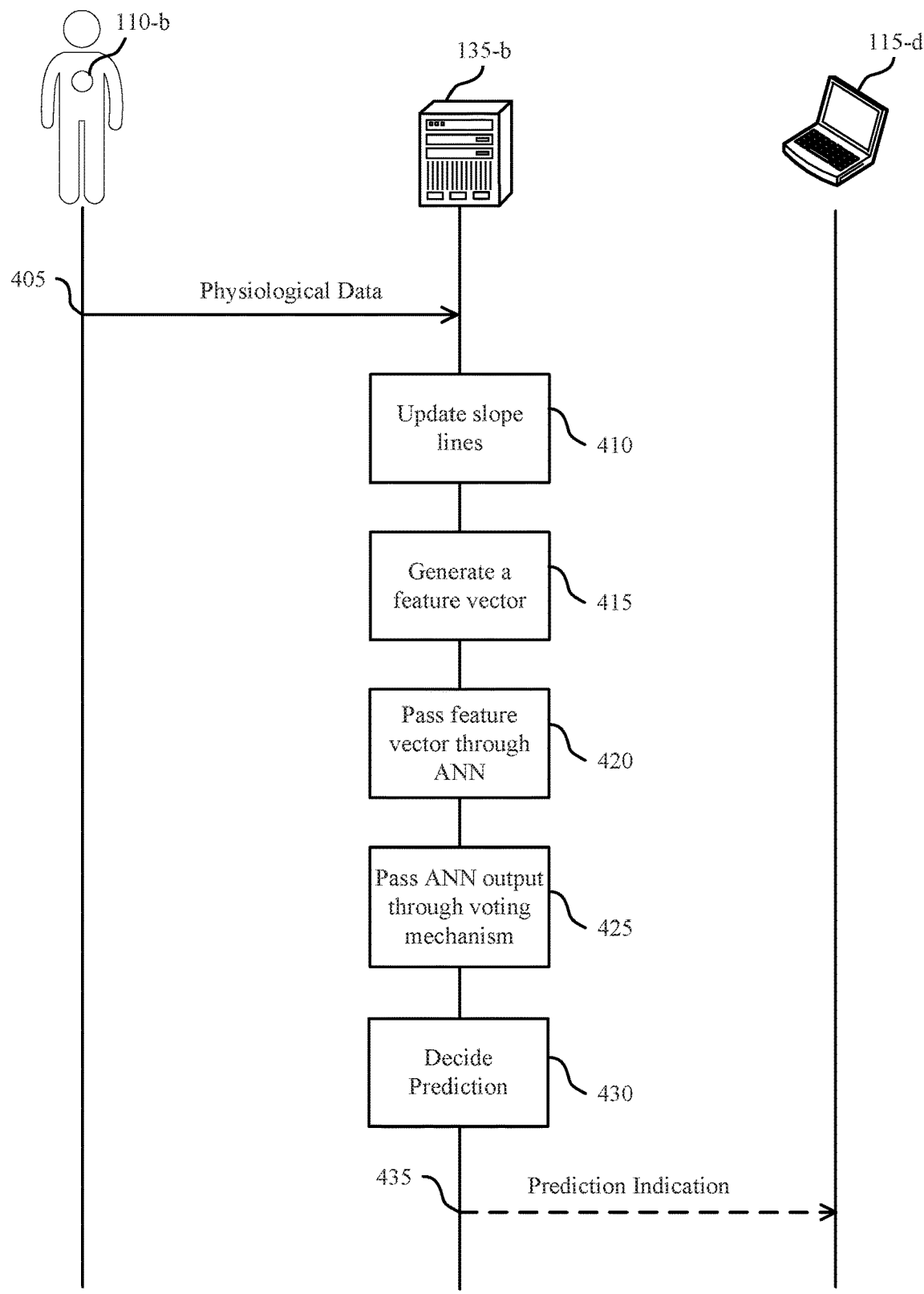
FIG. 4 illustrates an example of a process flow that supports prediction and reporting of medical events in accordance with aspects of the present disclosure.

FIG. 4 illustrates an example of a process flow 400 that supports prediction and reporting of medical events in accordance with aspects of the present disclosure. In some examples, process flow 400 may implement aspects of wireless patient monitoring system 100. In some examples, process flow 400 may include medical device 110-*b*, medical data server 135-*b*, and computing device 115-*d*, which may be respective examples of a medical device 110, central station 135, and computing device 115 as described with reference to FIGS. 1 and 2. The computing device 115-*d* may represent a device being used by a patient, clinician, or both. Alternative examples of the following may be implemented, where some steps are performed in a different order or not at all. Some steps may additionally include features not mentioned above. It should be noted that while the methods described herein describe physiological data being sent from a medical device 110-*b*, the methods may be further utilized with physiological data or non-physiological data from other sources without deviating from the scope of the present disclosure. Further, while the methods described herein describe predicting whether or not a medical event will occur, the methods may further describe whether or not other types of events will occur (e.g., if using non-physiological data).

At 405, medical device 110-*b* may transmit physiological data associated with one or more measurements (e.g., SpO2 measurements and/or respiration rate measurements) by medical device 110-*b*, and the medical data server 135-*b* may receive the physiological data. The medical data server 135-*b* may perform compression on the received physiological data so that the received physiological encompasses fewer data points (e.g., via averaging).

At 410, medical data server 135-*b* may update one or more slope lines (e.g., trend lines) associated with the physiological data. For instance, the one or more slopes lines may be derived based on performing a linear regression over the physiological data (compressed or uncompressed) for each time domain of one or more time domains. The time domains may overlap with each other or may be disjoint from each other.

At 415, medical data server 135-*b* may generate a feature vector from the physiological data. For instance, the feature vector may be composed of one or more most current data points (e.g., a different data point, all corresponding to the same time, for each type of measurement) and the one or more slopes corresponding to each of the most current data points.

At 420, medical data server 135-*b* may pass the feature vector through an ANN.

At 425, medical data server 135-*b* may pass the ANN output, which may be a predictive score, through a voting mechanism. The ANN output may be a binary vote (e.g., a positive or negative vote) or may be a number conveying the likelihood of a medical event occurring (e.g., a number on a scale between 1 to 5, where 1 is a negative vote, 2 is an unsure vote leaning negative, 3 is an undecided vote, 4 is an unsure vote leaning positive, and 5 is a positive vote). In other cases, the predictive score may be a time estimate, where the time estimate may be an estimated time until the medical event is predicted to occur.

At 430, medical data server 135-*b* may determine a prediction of whether or not a medical event will occur. The prediction may be based on a certain number of predictive scores of the total number of predictive scores being positive predictive scores. Additionally or alternatively, the prediction may be based on a certain number of predictive scores of the total number of predictive scores being negative predictive scores. Additionally or alternatively, the prediction may be based on a consecutive number of predictive scores (e.g., predictive scores that are output immediately after each other) being negative predictive scores. Additionally or alternatively, the prediction may be based on a consecutive number of predictive scores showing a downwards trend (e.g., decreasing monotonically) in estimations of time until a medical event will occur. Additionally or alternatively, the prediction may be based on a time-intercept associated with a certain number of predictive scores of the total number of predictive scores being within a time window.

At 435, medical data server 135-*b* may transmit a prediction indication (e.g., if medical data server 135-*b* determines a positive prediction). Computing device 115-*d* may receive the prediction indication. In some cases, computing device 115-*d* may perform an alerting function (e.g., may alert a clinician). Additionally or alternatively, computing device 115-*d* may provide a visualization indicating that the medical event will occur.

Figure 5:
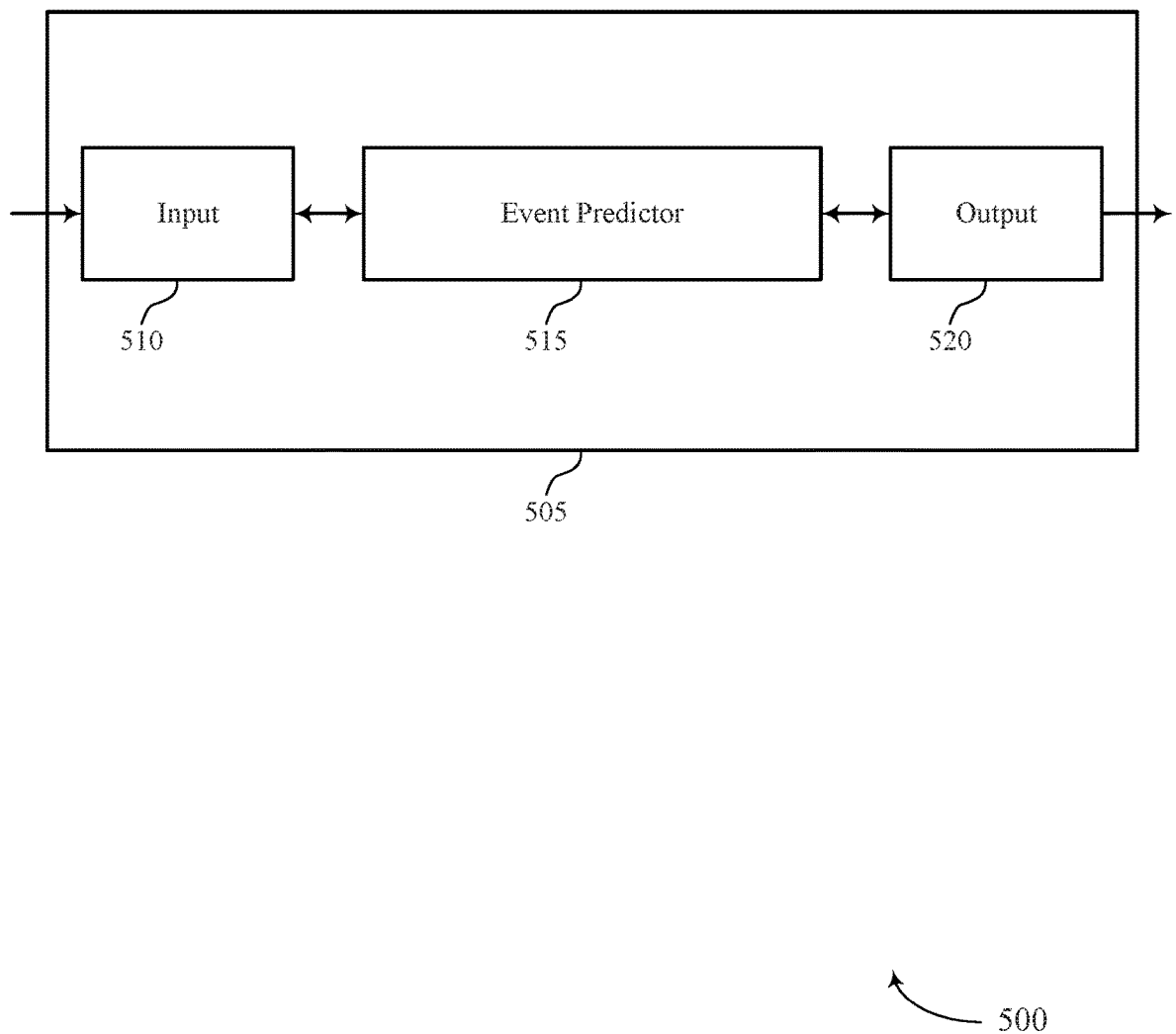
FIGS. 5 and 6 show block diagrams of devices that support prediction and reporting of medical events in accordance with aspects of the present disclosure.

FIG. 5 shows a block diagram 500 of a device 505 that supports prediction and reporting of medical events in accordance with aspects of the present disclosure. The device 505 may be an example of aspects of a medical data server as described herein. The device 505 may include an input 510, an event predictor 515, and an output 520. The device 505 may also include a processor. Each of these components may be in communication with one another (e.g., via one or more buses).

The event predictor 515 may receive real-time data (e.g., real-time physiological data) associated with one or more measurements by a medical device, update one or more slope lines based on past instances of the real-time data, generate a first feature vector based on the real-time data and the one or more slope lines, pass the first feature vector through an artificial neural network (ANN), identify a first output from the ANN including at least a first predictive score, and predict whether an event (e.g., a medical event) will occur at a time in the future based on the first predictive score. The event predictor 515 may be an example of aspects of the event predictor 810 described herein.

The event predictor 515, or its sub-components, may be implemented in hardware, code (e.g., software or firmware) executed by a processor, or any combination thereof. If implemented in code executed by a processor, the functions of the event predictor 515, or its sub-components may be executed by a general-purpose processor, a DSP, an application-specific integrated circuit (ASIC), a field programmable gate array (FPGA) or other programmable logic device, discrete gate or transistor logic, discrete hardware components, or any combination thereof designed to perform the functions described in the present disclosure.

The event predictor 515, or its sub-components, may be physically located at various positions, including being distributed such that portions of functions are implemented at different physical locations by one or more physical components. In some examples, the event predictor 515, or its sub-components, may be a separate and distinct component in accordance with various aspects of the present disclosure. In some examples, the event predictor 515, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

Figure 6:
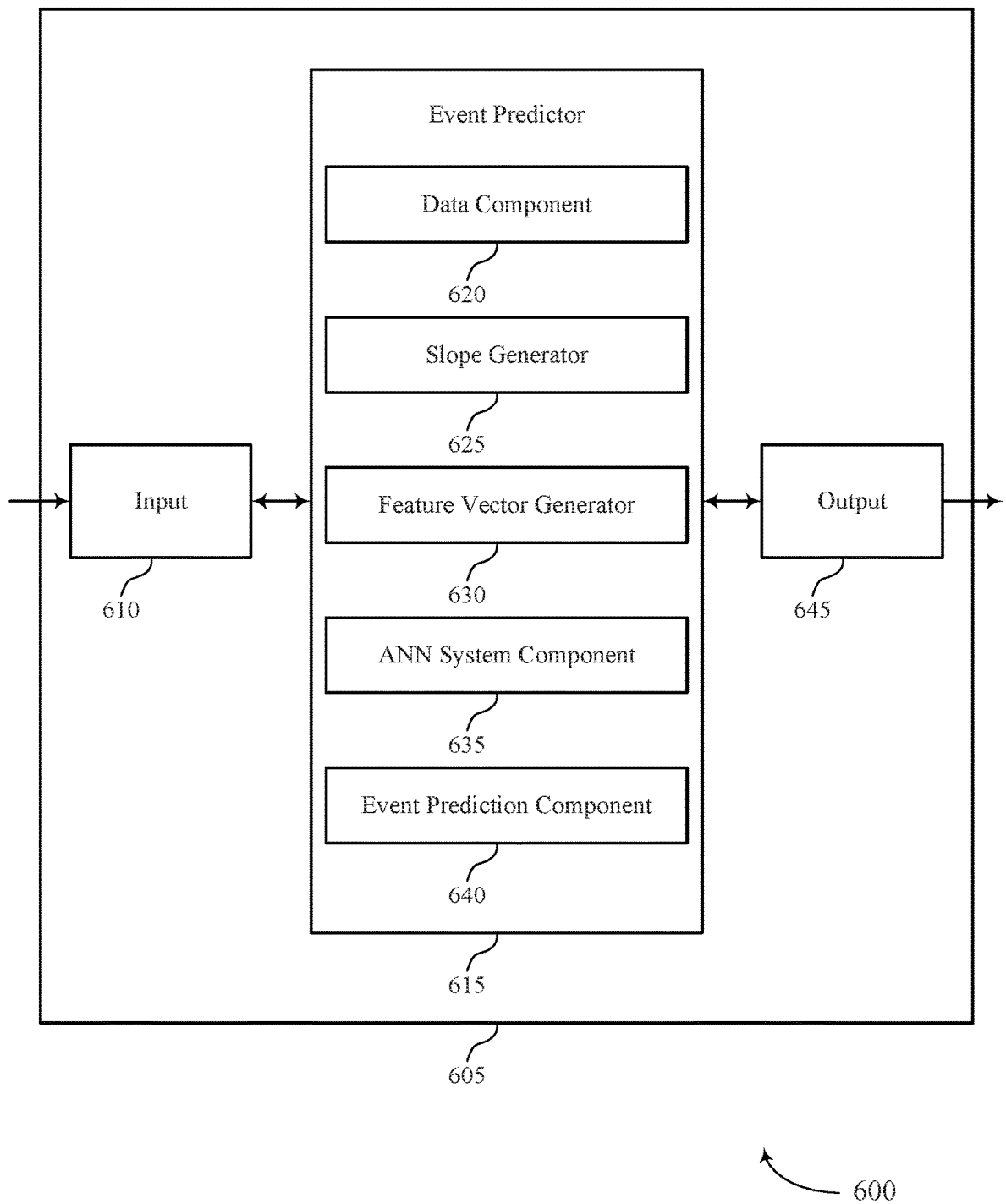

FIG. 6 shows a block diagram 600 of a device 605 that supports prediction and reporting of medical events in accordance with aspects of the present disclosure. The device 605 may be an example of aspects of a device 505 or a medical data server 135 as described herein. The device 605 may include an input 610, an event predictor 615, and an output 645. The device 605 may also include a processor. Each of these components may be in communication with one another (e.g., via one or more buses).

The event predictor 615 may be an example of aspects of the event predictor 515 as described herein. The event predictor 615 may include a data component 620, a slope generator 625, a feature vector generator 630, an ANN system component 635, and an event prediction component 640. The event predictor 615 may be an example of aspects of the event predictor 810 described herein.

The data component 620 may receive real-time data (e.g., physiological data) associated with one or more measurements by a medical device.

The slope generator 625 may update one or more slope lines based on past instances of the real-time data.

The feature vector generator 630 may generate a first feature vector based on the real-time data and the one or more slope lines.

The ANN system component 635 may pass the first feature vector through an artificial neural network (ANN) and identify a first output from the ANN including at least a first predictive score.

The event prediction component 640 may predict whether a medical event will occur at a time in the future based on the first predictive score.

Figure 7:
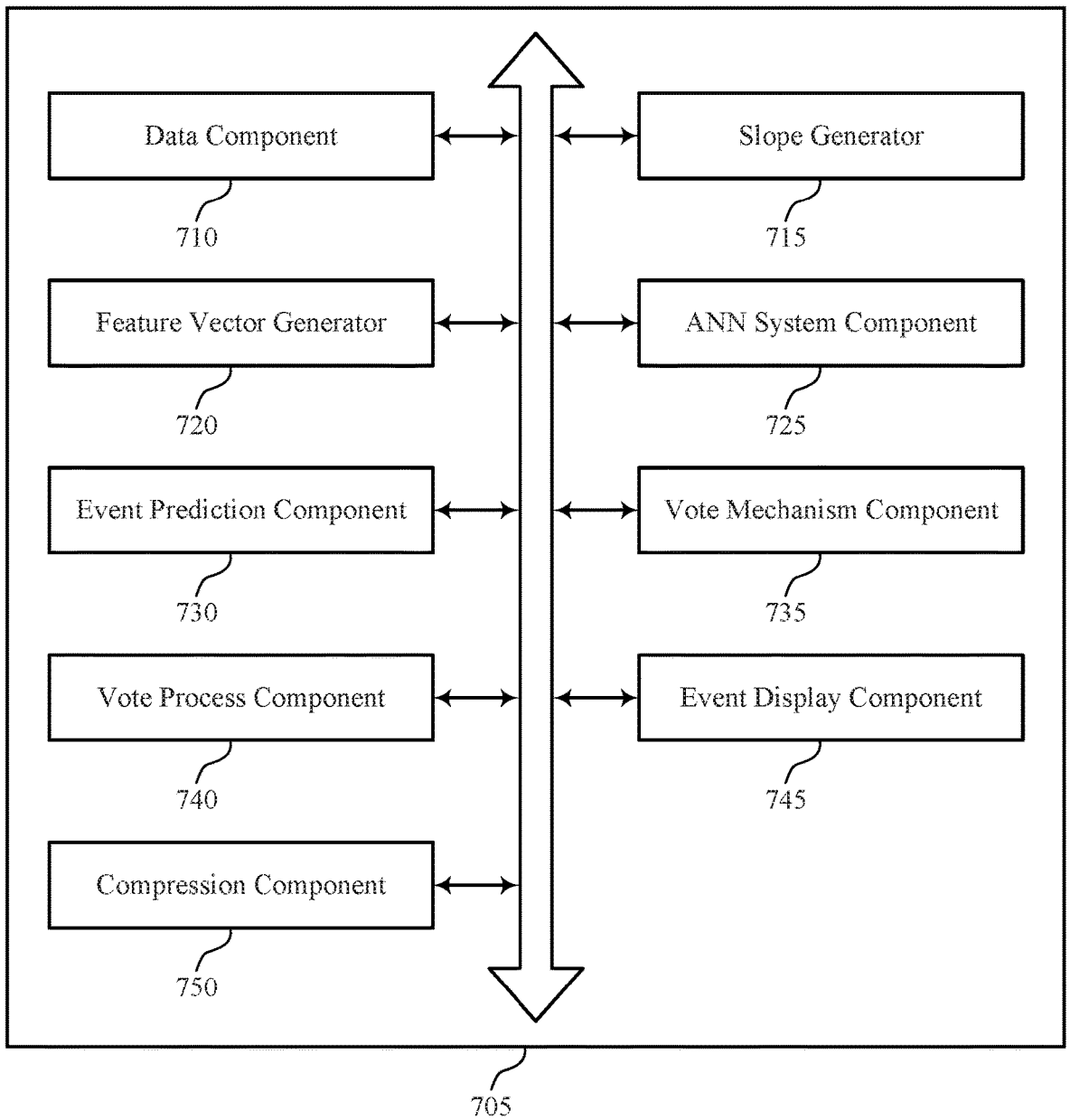
FIG. 7 shows a block diagram of an event predictor that supports prediction and reporting of medical events in accordance with aspects of the present disclosure.

FIG. 7 shows a block diagram 700 of an event predictor 705 that supports prediction and reporting of medical events in accordance with aspects of the present disclosure. The event predictor 705 may be an example of aspects of an event predictor 515, an event predictor 615, or an event predictor 810 described herein. The event predictor 705 may include a data component 710, a slope generator 715, a feature vector generator 720, an ANN system component 725, an event prediction component 730, a vote mechanism component 735, a vote process component 740, an event display component 745, and a compression component 750. Each of these modules may communicate, directly or indirectly, with one another (e.g., via one or more buses).

The data component 710 may receive real-time data associated with one or more measurements by a medical device. In some cases, the real-time data may be real-time physiological data and the physiological data may include ETCO2 data, respiration rate data. SpO2 data, heart rate data, or a combination thereof.

The slope generator 715 may update one or more slope lines based on past instances of the real-time data. In some examples, the slope generator 715 may perform one or more linear regressions over one or time domains, where each time domain is associated with a subset of the past instances of the real-time data. In some examples, the slope generator 715 may generate one or more trend lines based on performing the one or more linear regressions. In some examples, the slope generator 715 may determine slopes for each of the one or more trend lines. In some cases, the one or more time domains include a set of overlapping time domains. In some cases, the one or more time domains include a set of disjoint time domains.

The feature vector generator 720 may generate a first feature vector based on the real-time data and the one or more slope lines.

The ANN system component 725 may pass the first feature vector through an artificial neural network (ANN). In some examples, the ANN system component 725 may identify a first output from the ANN including at least a first predictive score. In some examples, the ANN system component 725 may identify one or more additional outputs of the ANN including one or more additional predictive scores. In some cases, the one or more additional outputs of the ANN are associated with data received at points later in time than the real-time data.

The event prediction component 730 may predict whether an event will occur at a time in the future based on the first predictive score. In some examples, the event prediction component 730 may predict whether the event will occur based on the voting mechanism output, where the voting mechanism output is based on the first predictive score and the one or more additional predictive scores. In some examples, the event prediction component 730 may predict whether the event will occur based on determining that the total number of predictive scores is above the minimum threshold. In some examples, the event prediction component 730 may predict that the event will occur based on a percentage of positive votes being above the threshold. In some examples, the event prediction component 730 may predict that the event will not occur based on a percentage of negative votes being above the threshold. In some examples, the event prediction component 730 may predict that the event will not occur based on determining that a number of consecutive predictive votes is above the threshold. In some cases, event prediction component 730 may predict that the event will occur based on determining that a predictive score of a set of consecutive predictive scores includes a lower time estimate than another predictive score of the set of consecutive predictive scores. In some cases, the event prediction component 730 may predict that the medical event will occur based on determining that an intercept is within a time window. In some cases, the event may be a medical event, such as a respiratory event.

The vote mechanism component 735 may pass the first predictive score through a voting mechanism. In some examples, the vote mechanism component 735 may identify an output from the voting mechanism. In some examples, the vote mechanism component 735 may pass the one or more additional predictive scores through the voting mechanism. In some examples, the vote mechanism component 735 may determine that a percentage of positive votes is above a threshold. In some examples, the vote mechanism component 735 may determine that a percentage of negative votes is above a threshold. In some examples, the vote mechanism component 735 may determine that the first predictive score and the one or more additional predictive scores has a time-based order. In some examples, the vote mechanism component 735 may determine that a number of consecutive predictive scores, including two or more of the first predictive score and the one or more additional predictive scores, include negative votes. In some examples, the vote mechanism component 735 may determine that the number of consecutive predictive scores is above a threshold. In some cases, the output from the voting mechanism includes a percentage, and where each predictive score of the first predictive score and the one or more additional predictive scores includes a positive vote or a negative vote. In some examples, the vote mechanism 735 may determine that at least one predictive score of a set of consecutive predictive scores, including two or more of the first predictive score and the one or more additional predictive scores, includes a lower time estimate than that of another predictive score of the set of consecutive predictive scores, where the first predictive score and the one or more additional predictive scores include time estimates. In some examples, the vote mechanism component 735 may determine an intercept associated with the first predictive score and the one or more additional predictive scores, where the first predictive score and the one or more additional predictive scores include time estimates, and determine that the intercept is within a time window.

The vote process component 740 may determine that a total number of predictive scores is above a minimum threshold, where the total number of predictive scores includes the first predictive score and the one or more additional predictive scores. In some examples, the vote process component 740 may determine to pass the first predictive score and the one or more additional predictive scores through the voting mechanism based on the first predictive score including a positive vote. In some examples, the vote process component 740 may determine to cease passing new predictive scores through the voting mechanism.

The event display component 745 may transmit, to a display, an indication that the event will occur based on predicting the event will occur at the time in the future.

The compression component 750 may receive a set of instances of the real-time data by the device over a period of time. In some examples, the compression component 750 may combine the set of instances of the real-time data into a single instance for the period of time.

Figure 8:
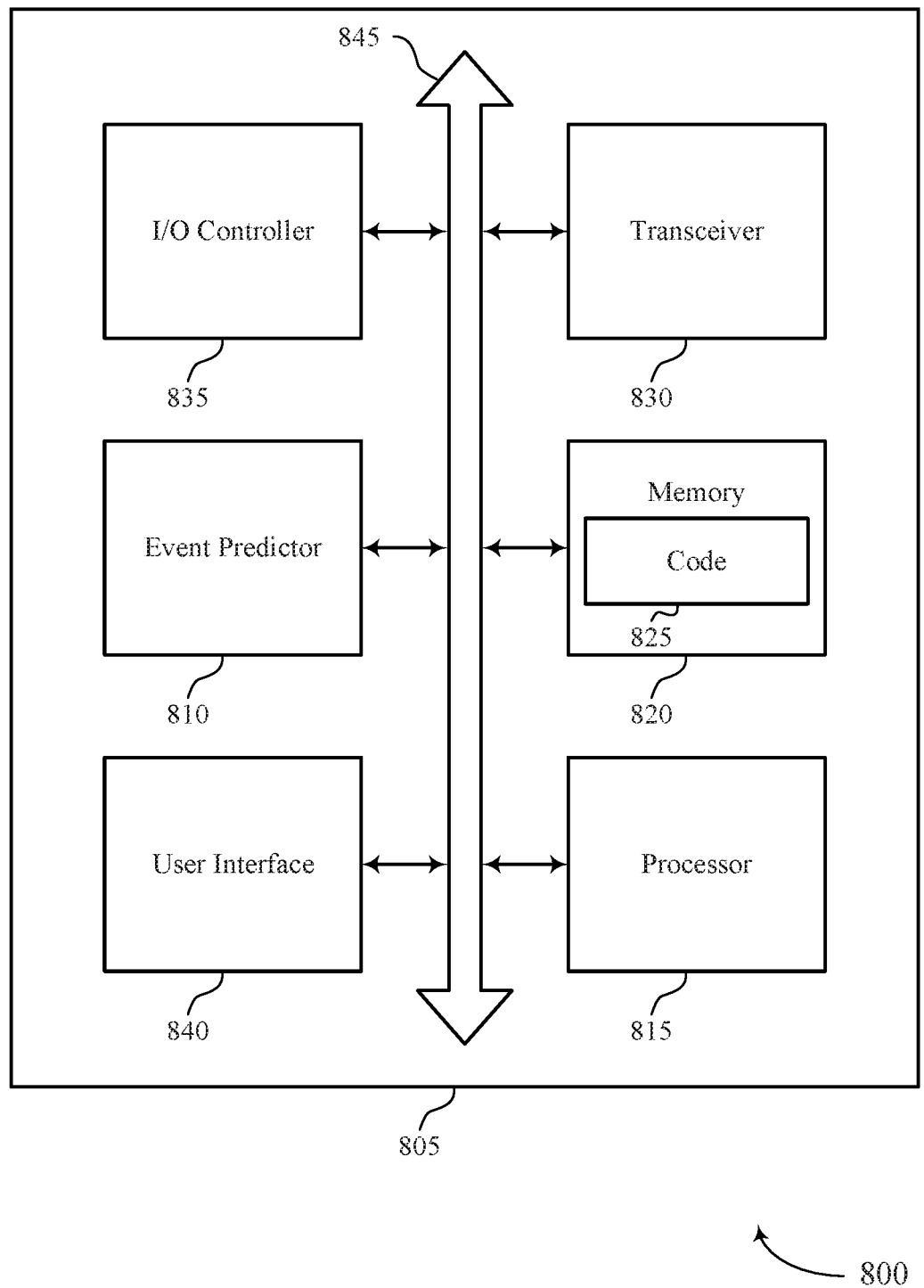
FIG. 8 shows a diagram of a system including a device that supports prediction and reporting of medical events in accordance with aspects of the present disclosure.

FIG. 8 shows a diagram of a system 800 including a device 805 that supports prediction and reporting of medical events in accordance with aspects of the present disclosure. The device 805 may be an example of or include the components of device 505, device 605, or a medical data server as described herein. The device 805 may include components for bi-directional voice and data communications including components for transmitting and receiving communications, including an event predictor 810, a processor 815, memory 820, a transceiver 830, an I/O controller 835, and an user interface 840. These components may be in electronic communication via one or more buses (e.g., bus 845).

The event predictor 810 may receive real-time data (e.g., real-time physiological data) associated with one or more measurements by a medical device, update one or more slope lines based on past instances of the real-time data, generate a first feature vector based on the real-time data and the one or more slope lines, pass the first feature vector through an artificial neural network (ANN), identify a first output from the ANN including at least a first predictive score, and predict whether an event (e.g., a medical event) will occur at a time in the future based on the first predictive score.

Processor 815 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, processor 815 may be configured to operate a memory array using a memory controller. In other cases, a memory controller may be integrated into processor 815. Processor 815 may be configured to execute computer-readable instructions stored in a memory to perform various functions (e.g., functions or tasks supporting prediction and reporting of medical events).

Memory 820 may include random access memory (RAM) and read-only memory (ROM). The memory 820 may store computer-readable, computer-executable software 825 including instructions that, when executed, cause the processor to perform various functions described herein. In some cases, the memory 820 may contain, among other things, a BIOS which may control basic hardware or software operation such as the interaction with peripheral components or devices.

Software 825 may include code to implement aspects of the present disclosure, including code to support video conferencing and virtual appointments. Software 825 may be stored in a non-transitory computer-readable medium such as system memory or other memory. In some cases, the software 825 may not be directly executable by the processor but may cause a computer (e.g., when compiled and executed) to perform functions described herein.

Transceiver 830 may communicate bi-directionally, via one or more antennas, wired, or wireless links as described above. For example, the transceiver 830 may represent a wireless transceiver and may communicate bi-directionally with another wireless transceiver. The transceiver 830 may also include a modem to modulate the packets and provide the modulated packets to the antennas for transmission, and to demodulate packets received from the antennas.

I/O controller 835 may manage input and output signals for device 805. I/O controller 835 may also manage peripherals not integrated into device 805. In some cases, I/O controller 835 may represent a physical connection or port to an external peripheral. In some cases, I/O controller 835 may utilize an operating system such as iOS®, ANDROID®, MS-DOS®, MS-WINDOWS®, OS/2®, UNIX®, LINUX®, or another known operating system. In other cases, I/O controller 835 may represent or interact with a modem, a keyboard, a mouse, a touchscreen, or a similar device. In some cases. I/O controller 835 may be implemented as part of a processor. In some cases, a user may interact with device 805 via I/O controller 835 or via hardware components controlled by I/O controller 835.

User interface 840 may enable a user to interact with device 805. In some embodiments, the user interface 840 may include an audio device, such as an external speaker system, an external display device such as a display screen, or an input device (e.g., remote control device interfaced with the user interface 840 directly or through the I/O controller module).

Figure 9:
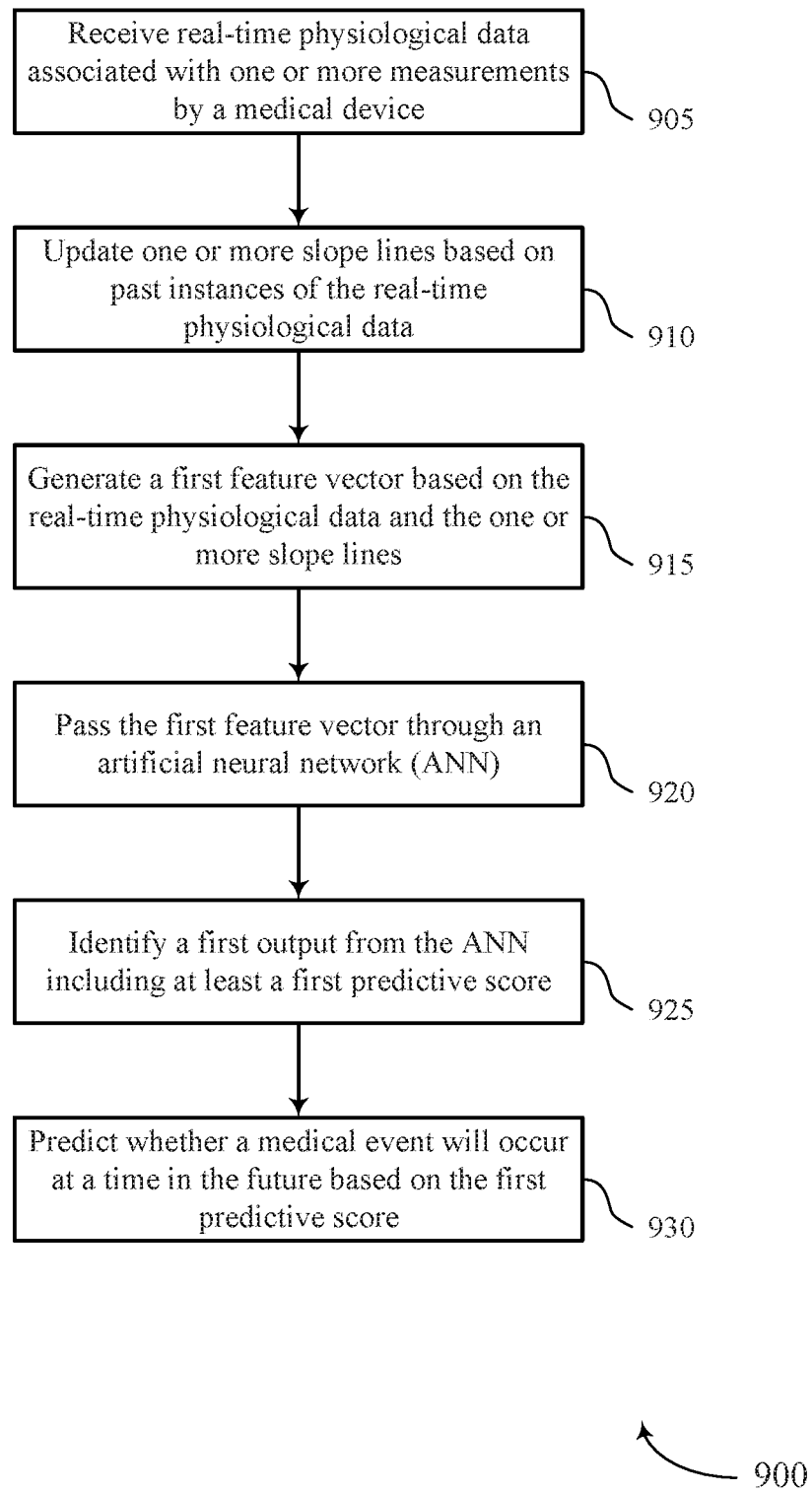
FIGS. 9 through 11 show flowcharts illustrating methods that support prediction and reporting of medical events in accordance with aspects of the present disclosure.

FIG. 9 shows a flowchart illustrating a method 900 that supports prediction and reporting of medical events in accordance with aspects of the present disclosure. The operations of method 900 may be implemented by a medical data server or its components as described herein. For example, the operations of method 900 may be performed by an event predictor as described with reference to FIGS. 5 through 8. In some examples, a medical data server may execute a set of instructions to control the functional elements of the medical data server to perform the functions described below. Additionally or alternatively, a medical data server may perform aspects of the functions described below using special-purpose hardware.

At 905, the medical data server may receive real-time physiological data associated with one or more measurements by a medical device. The operations of 905 may be performed according to the methods described herein. In some examples, aspects of the operations of 905 may be performed by a data component as described with reference to FIGS. 5 through 8.

At 910, the medical data server may update one or more slope lines based on past instances of the real-time physiological data. The operations of 910 may be performed according to the methods described herein. In some examples, aspects of the operations of 910 may be performed by a slope generator as described with reference to FIGS. 5 through 8.

At 915, the medical data server may generate a first feature vector based on the real-time physiological data and the one or more slope lines. The operations of 915 may be performed according to the methods described herein. In some examples, aspects of the operations of 915 may be performed by a feature vector generator as described with reference to FIGS. 5 through 8.

At 920, the medical data server may pass the first feature vector through an artificial neural network (ANN). The operations of 920 may be performed according to the methods described herein. In some examples, aspects of the operations of 920 may be performed by an ANN system component as described with reference to FIGS. 5 through 8.

At 925, the medical data server may identify a first output from the ANN including at least a first predictive score. The operations of 925 may be performed according to the methods described herein. In some examples, aspects of the operations of 925 may be performed by an ANN system component as described with reference to FIGS. 5 through 8.

At 930, the medical data server may predict whether a medical event will occur at a time in the future based on the first predictive score. The operations of 930 may be performed according to the methods described herein. In some examples, aspects of the operations of 930 may be performed by an event prediction component as described with reference to FIGS. 5 through 8.

Figure 10:
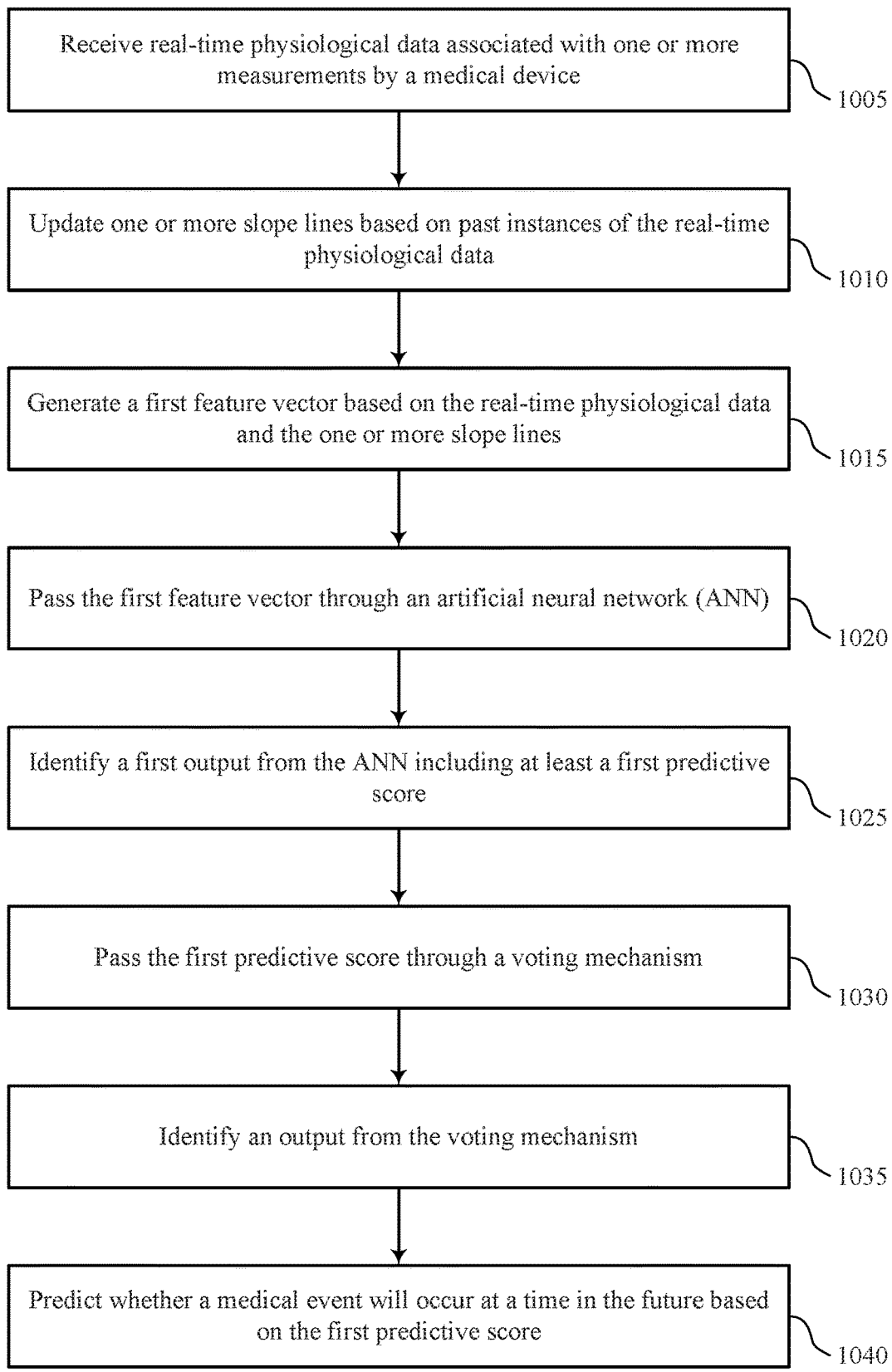

FIG. 10 shows a flowchart illustrating a method 1000 that supports prediction and reporting of medical events in accordance with aspects of the present disclosure. The operations of method 1000 may be implemented by a medical data server or its components as described herein. For example, the operations of method 1000 may be performed by an event predictor as described with reference to FIGS. 5 through 8. In some examples, a medical data server may execute a set of instructions to control the functional elements of the medical data server to perform the functions described below. Additionally or alternatively, a medical data server may perform aspects of the functions described below using special-purpose hardware.

At 1005, the medical data server may receive real-time physiological data associated with one or more measurements by a medical device. The operations of 1005 may be performed according to the methods described herein. In some examples, aspects of the operations of 1005 may be performed by a data component as described with reference to FIGS. 5 through 8.

At 1010, the medical data server may update one or more slope lines based on past instances of the real-time physiological data. The operations of 1010 may be performed according to the methods described herein. In some examples, aspects of the operations of 1010 may be performed by a slope generator as described with reference to FIGS. 5 through 8.

At 1015, the medical data server may generate a first feature vector based on the real-time physiological data and the one or more slope lines. The operations of 1015 may be performed according to the methods described herein. In some examples, aspects of the operations of 1015 may be performed by a feature vector generator as described with reference to FIGS. 5 through 8.

At 1020, the medical data server may pass the first feature vector through an artificial neural network (ANN). The operations of 1020 may be performed according to the methods described herein. In some examples, aspects of the operations of 1020 may be performed by an ANN system component as described with reference to FIGS. 5 through 8.

At 1025, the medical data server may identify a first output from the ANN including at least a first predictive score. The operations of 1025 may be performed according to the methods described herein. In some examples, aspects of the operations of 1025 may be performed by an ANN system component as described with reference to FIGS. 5 through 8.

At 1030, the medical data server may pass the first predictive score through a voting mechanism. The operations of 1030 may be performed according to the methods described herein. In some examples, aspects of the operations of 1030 may be performed by a vote mechanism component as described with reference to FIGS. 5 through 8.

At 1035, the medical data server may identify an output from the voting mechanism. The operations of 1035 may be performed according to the methods described herein. In some examples, aspects of the operations of 1035 may be performed by a vote mechanism component as described with reference to FIGS. 5 through 8.

At 1040, the medical data server may predict whether a medical event will occur at a time in the future based on the first predictive score. The operations of 1040 may be performed according to the methods described herein. In some examples, aspects of the operations of 1040 may be performed by an event prediction component as described with reference to FIGS. 5 through 8.

Figure 11:
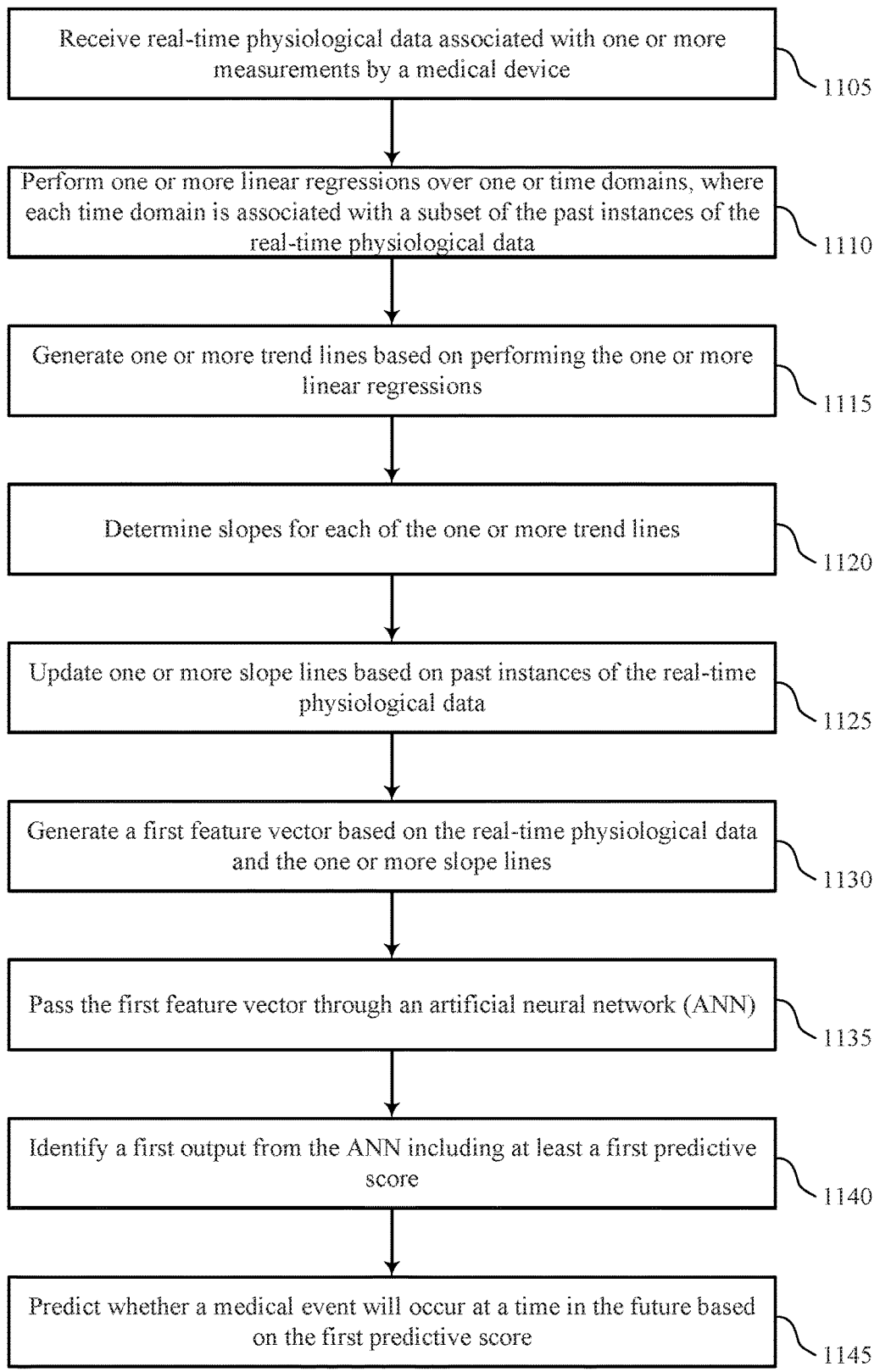

FIG. 11 shows a flowchart illustrating a method 1100 that supports prediction and reporting of medical events in accordance with aspects of the present disclosure. The operations of method 1100 may be implemented by a medical data server or its components as described herein. For example, the operations of method 1100 may be performed by an event predictor as described with reference to FIGS. 5 through 8. In some examples, a medical data server may execute a set of instructions to control the functional elements of the medical data server to perform the functions described below. Additionally or alternatively, a medical data server may perform aspects of the functions described below using special-purpose hardware.

At 1105, the medical data server may receive real-time physiological data associated with one or more measurements by a medical device. The operations of 1105 may be performed according to the methods described herein. In some examples, aspects of the operations of 1105 may be performed by a data component as described with reference to FIGS. 5 through 8.

At 1110, the medical data server may perform one or more linear regressions over one or time domains, where each time domain is associated with a subset of the past instances of the real-time physiological data. The operations of 1110 may be performed according to the methods described herein. In some examples, aspects of the operations of 1110 may be performed by a slope generator as described with reference to FIGS. 5 through 8.

At 1115, the medical data server may generate one or more trend lines based on performing the one or more linear regressions. The operations of 1115 may be performed according to the methods described herein. In some examples, aspects of the operations of 1115 may be performed by a slope generator as described with reference to FIGS. 5 through 8.

At 1120, the medical data server may determine slopes for each of the one or more trend lines. The operations of 1120 may be performed according to the methods described herein. In some examples, aspects of the operations of 1120 may be performed by a slope generator as described with reference to FIGS. 5 through 8.

At 1125, the medical data server may update one or more slope lines based on past instances of the real-time physiological data. The operations of 1125 may be performed according to the methods described herein. In some examples, aspects of the operations of 1125 may be performed by a slope generator as described with reference to FIGS. 5 through 8.

At 1130, the medical data server may generate a first feature vector based on the real-time physiological data and the one or more slope lines. The operations of 1130 may be performed according to the methods described herein. In some examples, aspects of the operations of 1130 may be performed by a feature vector generator as described with reference to FIGS. 5 through 8.

At 1135, the medical data server may pass the first feature vector through an artificial neural network (ANN). The operations of 1135 may be performed according to the methods described herein. In some examples, aspects of the operations of 1135 may be performed by an ANN system component as described with reference to FIGS. 5 through 8.

At 1140, the medical data server may identify a first output from the ANN including at least a first predictive score. The operations of 1140 may be performed according to the methods described herein. In some examples, aspects of the operations of 1140 may be performed by an ANN system component as described with reference to FIGS. 5 through 8.

At 1145, the medical data server may predict whether a medical event will occur at a time in the future based on the first predictive score. The operations of 1145 may be performed according to the methods described herein. In some examples, aspects of the operations of 1145 may be performed by an event prediction component as described with reference to FIGS. 5 through 8.

It should be noted that the methods described above describe possible implementations, and that the operations and the steps may be rearranged or otherwise modified and that other implementations are possible. Further, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, a FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims. "or" as used in a list of items (for example, a list of items prefaced by a phrase such as "at least one of" or "one or more of") indicates an inclusive list such that, for example, a list of at least one of A. B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for patient monitoring at a server, comprising:
   receiving, from a medical device and at the server, real-time physiological data associated with one or more measurements by the medical device coupled with a patient;
   updating, by the server, a plurality of trend lines based at least in part on past instances of the real-time physiological data and a current instance of the real-time physiological data;
   generating, by the server, a first feature vector, wherein the first feature vector comprises the current instance of the real-time received physiological data and a plurality of slope values of the plurality of trend lines;
   passing, by the server, the first feature vector that comprises the current instance of the real-time received physiological data and the plurality of slope values of the plurality of trend lines, through a trained artificial neural network (ANN) based at least in part on generating the first feature vector;
   identifying, by the server, a first output from the trained ANN comprising at least a first predictive score;
   predicting, by the server, whether a medical event for the patient will occur at a future time based at least in part on the first predictive score, wherein predicting whether the medical event will occur comprises:
     identifying one or more additional outputs of the trained ANN, the one or more additional outputs comprising one or more additional predictive scores;
     passing the first predictive score and the one or more additional predictive scores through a voting mechanism; and
     predicting whether the medical event will occur based at least in part on an output from the voting mechanism, wherein the output from the voting mechanism is based at least in part on the first predictive score and the one or more additional predictive scores; and
   transmitting, from the server and to a display, an indication of whether the medical event for the patient will occur at the future time based at least in part on the output from the voting mechanism.

2. The method of claim 1, further comprising:
   determining that a total number of predictive scores is above a minimum threshold, wherein the total number of predictive scores comprises the first predictive score and the one or more additional predictive scores; and
   predicting whether the medical event will occur based at least in part on the determining that the total number of predictive scores is above the minimum threshold.

3. The method of claim 1, wherein each predictive score of the first predictive score and the one or more additional predictive scores comprises a positive vote or a negative vote.

4. The method of claim 3, further comprising:
   determining to pass the first predictive score and the one or more additional predictive scores through the voting mechanism based at least in part on the first predictive score comprising the positive vote.

5. The method of claim 4, wherein predicting whether the medical event will occur further comprises:
   determining that a percentage of positive votes is above a threshold; and
   predicting that the medical event will occur based at least in part on the percentage of positive votes being above the threshold.

6. The method of claim 4, wherein predicting whether the medical event will occur further comprises:
   determining that a percentage of negative votes is above a threshold;
   determining to cease passing new predictive scores through the voting mechanism; and
   predicting that the medical event will not occur based at least in part on the percentage of negative votes being above the threshold.

7. The method of claim 4, wherein predicting whether the medical event will occur further comprises:
   determining that the first predictive score and the one or more additional predictive scores have a time-based order;

determining that a number of consecutive predictive scores, comprising two or more of the first predictive score and the one or more additional predictive scores, comprise negative votes;

determining that the number of consecutive predictive scores is above a threshold;

determining to cease passing new predictive scores through the voting mechanism; and predicting that the medical event will not occur based at least in part on the determining that the number of consecutive predictive scores is above the threshold.

8. The method of claim 1, further comprising:

determining that the first predictive score and the one or more additional predictive scores have a time-based order, wherein the first predictive score and the one or more additional predictive scores comprise time estimates;

determining that at least one predictive score of a set of consecutive predictive scores, comprising two or more of the first predictive score and the one or more additional predictive scores, comprises a lower time estimate than that of another predictive score of the set of consecutive predictive scores; and predicting that the medical event will occur based at least in part on the determining that the at least one predictive score of the set of consecutive predictive scores comprises the lower time estimate.

9. The method of claim 1, further comprising:

determining an intercept associated with the first predictive score and the one or more additional predictive scores, wherein the first predictive score and the one or more additional predictive scores comprise time estimates;

determining that the intercept is within a time window; and predicting the medical event will occur based at least in part on the determining that the intercept is within the time window.

10. The method of claim 1, further comprising:

transmitting, to the display, an indication that the medical event will occur based at least in part on predicting the medical event will occur at the future time.

11. The method of claim 1, further comprising:

performing one or more linear regressions over one or more time domains, wherein each time domain is associated with a subset of the past instances of the real-time physiological data to generate the plurality of trend lines; and determining a respective slope value of each trend line of the plurality of trend lines.

12. The method of claim 11, wherein the one or more time domains comprise a plurality of overlapping time domains.

13. The method of claim 11, wherein the one or more time domains comprise a plurality of disjoint time domains.

14. The method of claim 1, wherein the medical event comprises a respiratory event.

15. The method of claim 1, wherein the real-time physiological data comprises end-tidal carbon dioxide (ETC02) data, respiration rate data, pulse oximetry (SpO2) data, heart rate data, or a combination thereof.

16. An apparatus for patient monitoring at a server, comprising:

one or more processors;

memory in electronic communication with the one or more processors; and instructions stored in the memory and executable by the one or more processors to cause the apparatus to:

receive, from a medical device and at the server, real-time physiological data associated with one or more measurements by the medical device coupled with a patient;

update, by the server, a plurality of trend lines based at least in part on past instances of the real-time physiological data and a current instance of the real-time physiological data;

generate, by the server, a first feature vector, wherein the first feature vector comprises the current instance of the real-time received physiological data and a plurality of slope values of the plurality of trend lines;

pass, by the server, the first feature vector that comprises the current instance of the real-time received physiological data and the plurality of slope values of the plurality of trend lines, through a trained artificial neural network (ANN) based at least in part on generating the first feature vector;

identify, by the server, a first output from the trained ANN comprising at least a first predictive score;

predict, by the server, whether a medical event for the patient will occur at a future time based at least in part on the first predictive score, including:

identifying one or more additional outputs of the trained ANN, the one or more additional outputs comprising one or more additional predictive scores;

passing the first predictive score and the one or more additional predictive scores through a voting mechanism; and predicting whether the medical event will occur based at least in part on an output from the voting mechanism, wherein the output from the voting mechanism is based at least in part on the first predictive score and the one or more additional predictive scores; and transmit, from the server and to a display, an indication of whether the medical event for the patient will occur at the future time based at least in part on the output from the voting mechanism.

17. A non-transitory computer-readable medium storing code for patient monitoring at a server, the code comprising instructions executable by one or more processors to:

receive, from a medical device and at the server, real-time physiological data associated with one or more measurements by the medical device coupled with a patient;

update, by the server, a plurality of trend lines based at least in part on past instances of the real-time physiological data and a current instance of the real-time physiological data;

generate, by the server, a first feature vector of, wherein the first feature vector comprises the current instance of the real-time received physiological data and a plurality of slope values of the plurality of trend lines;

pass, by the server, the first feature vector that comprises the current instance of the real-time received physiological data and the plurality of slope values of the plurality of trend lines, through a trained artificial neural network (ANN) based at least in part on generating the first feature vector;

identifying, by the server, a first output from the trained ANN comprising at least a first predictive score;

predict, by the server, whether a medical event for the patient will occur at a future time based at least in part on the first predictive score, including:

identifying one or more additional outputs of the trained ANN, the one or more additional outputs comprising one or more additional predictive scores;

passing the first predictive score and the one or more additional predictive scores through a voting mechanism; and predicting whether the medical event will occur based at least in part on an output from the voting mechanism, wherein the output from the voting mechanism is based at least in part on the first predictive score and the one or more additional predictive scores; and transmit, from the server and to a display, an indication of whether the medical event for the patient will occur at the future time based at least in part on the output from the voting mechanism.

18. A method for event prediction at a server, comprising:

receiving, from a device and at the server, real-time data associated with one or more measurements by the device coupled with a user;

updating, by the server, a plurality of trend lines based at least in part on past instances of the real-time data and a current instance of the real-time data;

generating, by the server, a first feature vector, wherein the first feature vector comprises the current instance of the real-time received data and a plurality of slope values of the plurality of trend lines;

passing, by the server, the first feature vector that comprises the current instance of the real-time received data and the plurality of slope values of the plurality of trend lines, through a trained artificial neural network (ANN) based at least in part on generating the first feature vector;

identifying, by the server, a first output from the trained ANN comprising at least a first predictive score;

predicting, by the server, whether an event for the user will occur at a future time based at least in part on the first predictive score, wherein predicting whether the event will occur comprises:

identifying one or more additional outputs of the trained ANN, the one or more additional outputs comprising one or more additional predictive scores;

passing the first predictive score and the one or more additional predictive scores through a voting mechanism; and predicting whether the event will occur based at least in part on an output from the voting mechanism, wherein the output from the voting mechanism is based at least in part on the first predictive score and the one or more additional predictive scores; and transmitting, from the server and to a display, an indication of whether the event for the user will occur at the future time based at least in part on the output from the voting mechanism.

\* \* \* \* \*